US012786313B2

(12) United States Patent
Horelik et al.

(10) Patent No.: US 12,786,313 B2
(45) Date of Patent: Nov. 3, 2026

(54) UNMANNED AERIAL VEHICLE EMERGENCY DISPATCH AND DIAGNOSTICS DATA APPARATUS, SYSTEMS AND METHODS

(71) Applicant: RAPIDSOS, INC., New York, NY (US)

(72) Inventors: Nicholas Edward Horelik, Long Island City, NY (US); Michael John Martin, New York, NY (US)

(73) Assignee: RapidSOS, Inc., New York, NY (US)

( * ) Notice: Subject to any disclaimer, the term of this patent is extended or adjusted under 35 U.S.C. 154(b) by 5 days.

(21) Appl. No.: 19/004,475

(22) Filed: Dec. 30, 2024

(65) Prior Publication Data

US 2025/0203007 A1 Jun. 19, 2025

Related U.S. Application Data

(63) Continuation of application No. 16/845,700, filed on Apr. 10, 2020, now Pat. No. 12,184,803.

(51) Int. Cl.

| | |
|---|---|
| ***G05D 1/00*** | (2024.01) |
| ***A61K 31/137*** | (2006.01) |
| ***A61M 5/20*** | (2006.01) |
| ***A61N 1/39*** | (2006.01) |
| ***B64U 10/13*** | (2023.01) |
| ***G05D 1/46*** | (2024.01) |
| ***H04M 3/51*** | (2006.01) |
| *B64U 101/21* | (2023.01) |
| *B64U 101/31* | (2023.01) |
| *B64U 101/47* | (2023.01) |

(Continued)

(52) U.S. Cl.
CPC ......... *H04M 3/5116* (2013.01); *A61K 31/137* (2013.01); *A61M 5/20* (2013.01); *A61N 1/3904* (2017.08); *B64U 10/13* (2023.01); *G05D 1/101* (2013.01); *G05D 1/46* (2024.01); *H04M 3/5133* (2013.01); *B64U 2101/21* (2023.01); *B64U 2101/31* (2023.01); *B64U 2101/47* (2023.01); *B64U 2101/55* (2023.01); *B64U 2101/64* (2023.01); *B64U 2201/10* (2023.01); *G05D 2109/20* (2024.01)

(58) Field of Classification Search
None
See application file for complete search history.

(56) References Cited

U.S. PATENT DOCUMENTS

2017/0092109 A1* 3/2017 Trundle .................. B60L 53/36
2017/0131727 A1* 5/2017 Kurdi .................. G05D 1/0027
(Continued)

*Primary Examiner* — Davin Seol
(74) *Attorney, Agent, or Firm* — Cygan Law Offices PC; Joseph T. Cygan

(57) ABSTRACT

A disclosed method includes monitoring a plurality of emergency event queues at an emergency network entity; determining that an emergency event in one of the emergency event queues corresponds to an emergency type that can be responded to using an unmanned aerial vehicle; determining that an unmanned aerial vehicle is available that has capabilities corresponding to the emergency type; establishing an unmanned aerial vehicle control link between the unmanned aerial vehicle and the emergency network entity; and deploying the unmanned aerial vehicle to the emergency event location and providing data from the unmanned aerial vehicle on a display of the emergency network entity.

20 Claims, 15 Drawing Sheets

(51) Int. Cl.

| | |
|---|---|
| *B64U 101/55* | (2023.01) |
| *B64U 101/64* | (2023.01) |
| *G05D 109/20* | (2024.01) |

(56) References Cited

U.S. PATENT DOCUMENTS

| | | | | |
|---|---|---|---|---|
| 2018/0093769 | A1* | 4/2018 | Sequeira | G01S 13/888 |
| 2018/0160316 | A1* | 6/2018 | Byrne | G08B 25/10 |
| 2018/0327091 | A1* | 11/2018 | Burks | B64U 50/13 |
| 2019/0228630 | A1* | 7/2019 | Gillum | G01S 5/0231 |
| 2019/0295428 | A1* | 9/2019 | Holmgren | G08G 5/57 |

* cited by examiner

UNMANNED AERIAL VEHICLE EMERGENCY DISPATCH AND DIAGNOSTICS DATA APPARATUS, SYSTEMS AND METHODS

CROSS-REFERENCE TO RELATED APPLICATIONS

The present application is a Divisional of U.S. patent application Ser. No. 16/845,700, filed Apr. 10, 2020, issuing as U.S. Pat. No. 12,184,803 on Dec. 12, 2024, which claimed priority to U.S. Provisional Patent Application No. 62/832,266, filed Apr. 10, 2019 entitled "AUTOMATED EMERGENCY DISPATCH OF UNMANNED AERIAL VEHICLES (UAVS)" which is hereby incorporated by reference herein in its entirety, and which is assigned to the same assignee as the present application.

FIELD OF THE DISCLOSURE

The present disclosure relates generally to emergency calls, enhanced 9-1-1 (E911) and next generation 9-1-1 (NG911) emergency networks, and more particularly, to use of unmanned aerial vehicles (UAVs) for acquisition of emergency event data for use in responding to emergencies.

BACKGROUND

Emergency networks which may also be referred to as emergency dispatch centers (EDC) including public safety answering points (PSAPs), utilize various enhanced 9-1-1 (E911) or next generation 9-1-1 (NG911) emergency network infrastructures which provide interconnection to the Internet protocol (IP) domain. An emergency network refers to an entity that may receive an emergency call or an emergency alert and coordinate emergency assistance. An emergency network may be owned and operated by a public organization run by a municipality, county or city, or by a private organization such as a corporation or college campus. Emergency assistance provided can include medical, caregivers, firefighting, police, military, paramilitary, border patrol, lifeguard, security services, or any combination thereof. These personnel may be referred to as "Emergency Service Providers" (ESPs) or "emergency responders," or "responders." In existing systems ESPs or responders are dispatched by dispatch operators who communicate with responders via radio dispatch systems.

In many emergency scenarios, a rapid response significantly increases the likelihood of a successful outcome. For example, rapidly providing certain treatments or responses (e.g., delivery of insulin to a diabetic patient, rescue protocols in the case of a fire, etc.) can dramatically increase the likelihood of survival or beneficial outcome. While existing technologies enable the dispatch of certain emergency resources, in many cases additional information is needed before identifying the specific resources necessary (e.g., a specific medical device, drug, etc.) and/or the manner in which such resources should be dispatched (e.g., the specific location of a fire, accident, etc.). Additionally, in certain scenarios such emergencies may occur in remote or inaccessible locations which may be difficult to reach by human responders in order to collect such information.

BRIEF DESCRIPTION OF THE DRAWINGS

FIG. 8A shows UAV information at initial UAV deployment and FIG. 8B shows UAV information upon the UAV arriving at an emergency location.

DETAILED DESCRIPTION

Figure 1:
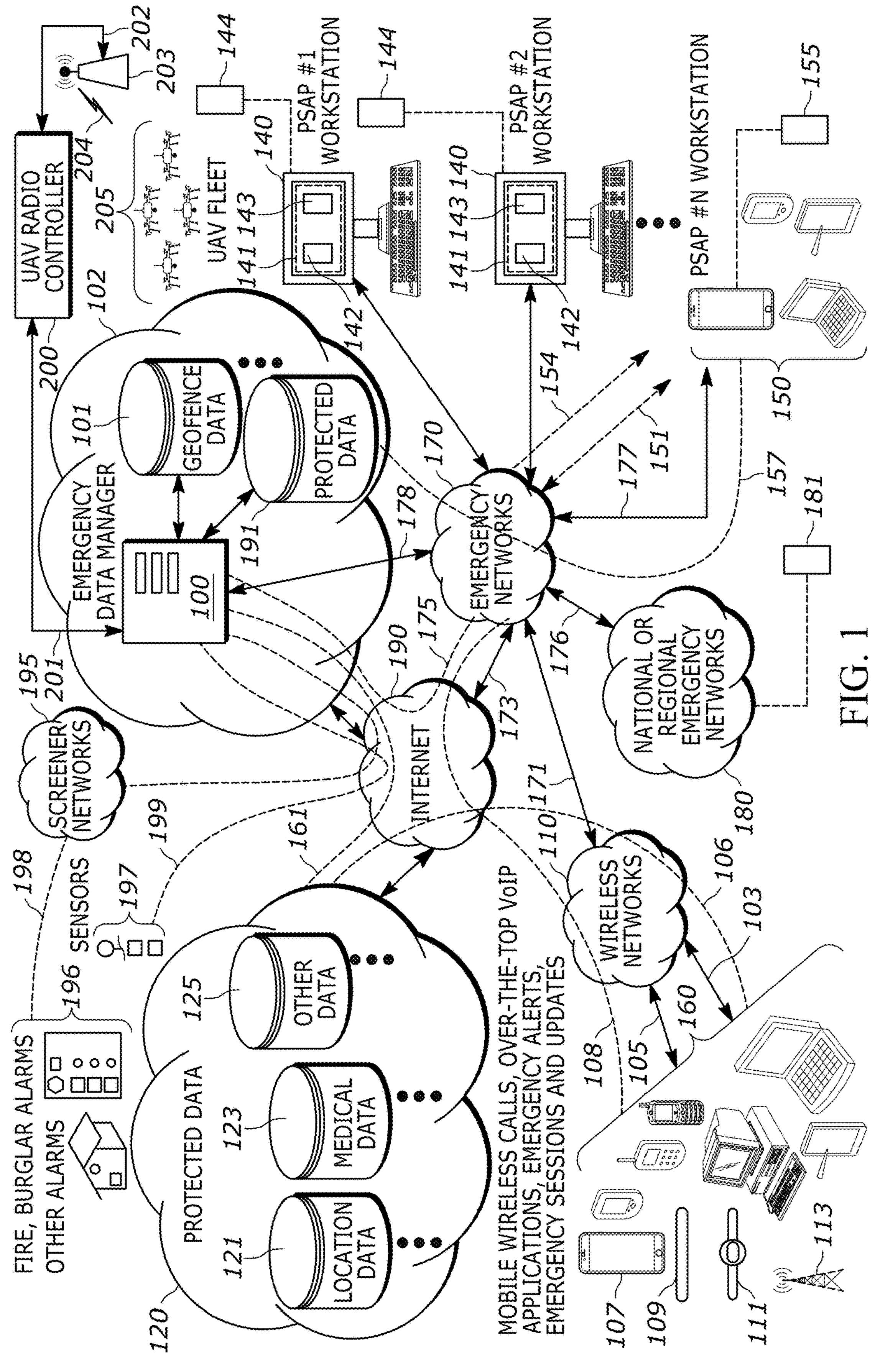
FIG. 1 is a diagram illustrating an emergency data manager in communication with various emergency networks, an unmanned aerial vehicle (UAV) radio controller and a UAV fleet in accordance with various embodiments.

Briefly, the present disclosure provides systems, apparatuses and methods for deploying unmanned aerial vehicles to emergency locations to conduct surveillance, or to bring critical medical equipment and instructions, in situations where emergency responders would not be able to get to the emergency location as quickly. The disclosed systems, apparatuses and methods are operative to deploy the unmanned aerial vehicles automatically.

Upon receiving an emergency notification, the described apparatuses and systems can rapidly dispatch one or more UAVs to the location of the emergency. Such UAVs can collect and transmit audio/visual content and/or other information. Such content can be analyzed to identify further aspects of the ongoing emergency. Based on such determinations, further UAVs (e.g., those carrying certain medical/rescue equipment, drugs, etc.) and/or other emergency resources can be dispatched. In doing so, the status of an ongoing emergency can be rapidly determined, and appropriate emergency resources can be dispatched efficiently, even in scenarios occurring at remote, dangerous, or inaccessible locations.

One disclosed method includes monitoring an emergency event queue at an emergency network entity; determining that an emergency event in the emergency event queue corresponds to an emergency type that can be responded to using an unmanned aerial vehicle; determining that an unmanned aerial vehicle is available that has capabilities corresponding to the emergency type; establishing an unmanned aerial vehicle control link between the unmanned aerial vehicle and the emergency network entity; deploying the unmanned aerial vehicle to the emergency event location; and providing data from the unmanned aerial vehicle on a display of the emergency network entity.

The method may further include sending the emergency location to the unmanned aerial vehicle from the emergency network entity using the control link. Deploying the unmanned aerial vehicle to the emergency location may further include auto-navigating by the unmanned aerial vehicle to the emergency event location using the emergency location and an onboard location module. Determining that an unmanned aerial vehicle is available that has capabilities corresponding to the emergency type, may further include determining that the emergency type is a medical emergency; and deploying the unmanned aerial vehicle with a medical equipment payload to the emergency event location. Deploying the unmanned aerial vehicle with a medical equipment payload to the emergency location may further include deploying the unmanned aerial vehicle to the emergency location with the medical equipment payload being an automated external defibrillator (AED) or an epinephrine auto-injector. Determining that an unmanned aerial vehicle is available that has capabilities corresponding to the emergency type, may further include determining that the emergency type requires visual surveillance; and deploying the unmanned aerial vehicle with a camera to the emergency location. Determining that an unmanned aerial vehicle is available that has capabilities corresponding to the emergency type, may further include determining that the emergency type is a medical emergency and requires visual surveillance; deploying a first unmanned aerial vehicle with a medical equipment payload to the emergency location; and deploying a second unmanned aerial vehicle with a camera to the emergency location. Determining that an unmanned aerial vehicle is available that has capabilities corresponding to the emergency type, may further include determining that the emergency type requires location of a radio signal source; and deploying at least two unmanned aerial vehicles to a region in which to search for the radio signal source, with each unmanned aerial vehicle having a radio receiver operative to perform a coordinated location detection operation based on detection of the radio signal source. The method may further include sending emergency location to at least two unmanned aerial vehicles from the emergency network entity using the control link, where the location was obtained from a gunshot detection system; deploying a first unmanned aerial vehicle to the emergency location; and deploying the second unmanned aerial vehicle to a perimeter location within a predetermined distance from the emergency location.

A disclosed apparatus includes at least one emergency network manager operative to connect to at least one emergency network entity via an Internet connection. The at least one emergency network manager operative is to: monitor an emergency queue at the at least one emergency network entity; determine that an emergency in the emergency queue corresponds to an emergency type that can be responded to using an unmanned aerial vehicle; and determine that an unmanned aerial vehicle is available that has capabilities corresponding to the emergency type. An unmanned aerial vehicle dispatch controller is operatively coupled to the at least one emergency network manager, and to an unmanned aerial vehicle radio controller. The unmanned aerial vehicle controller is operative to: establish an unmanned aerial vehicle control link between an unmanned aerial vehicle and the at least one emergency network entity via the Internet connection; and deploy the unmanned aerial vehicle to the emergency location and provide data from the unmanned aerial vehicle on a display of the at least one emergency network entity. The at least one emergency network manager may be further operative to send emergency location data to the unmanned aerial vehicle from the emergency network entity using the control link.

A disclosed system includes the apparatus and at least one unmanned aerial vehicle that has an onboard location module. The at least one unmanned aerial vehicle is operative to auto-navigate to the emergency location using the emergency location data and an onboard location module.

Another system includes the apparatus and at least one unmanned aerial vehicle with a medical equipment payload. The at least one emergency network manager is further operative to: determine that the emergency type is a medical emergency; and control the unmanned aerial vehicle dispatch controller to deploy the unmanned aerial vehicle to the emergency location. The medical equipment payload may be an automated external defibrillator (AED) or an epinephrine auto-injector.

Another disclosed system includes the apparatus and at least one unmanned aerial vehicle having a camera. The at least one emergency network manager is further operative to: determine that the emergency type requires visual surveillance; and control the unmanned aerial vehicle dispatch controller to deploy the unmanned aerial vehicle to the emergency location.

Another disclosed system includes the apparatus, at least one unmanned aerial vehicle with a medical equipment payload, and at least a second unmanned aerial vehicle with a camera. The at least one emergency network manager is further operative to: determine that the emergency type is a medical emergency and requires visual surveillance; control the unmanned aerial vehicle dispatch controller to deploy the first unmanned aerial vehicle to the emergency location; and control the unmanned aerial vehicle dispatch controller to deploy the second unmanned aerial vehicle to the emergency location.

Another disclosed system includes the apparatus and at least two unmanned aerial vehicles each with a radio receiver additional to an unmanned aerial vehicle radio control receiver. The at least two unmanned aerial vehicles are operative to perform a coordinated radio source location detection operation based on detection of a radio signal using the radio receiver. The at least one emergency network manager is further operative to: determine that the emergency type requires locating the source of a radio signal; and control the unmanned aerial vehicle dispatch controller to deploy the at least two unmanned aerial vehicles to a region in which to search for the radio signal source by performing a coordinated location detection operation based on detection of the radio signal.

Another disclosed system includes the apparatus and at least two unmanned aerial vehicles each with a camera. The at least one emergency network manager is further operative to: send emergency location data to each of the at least two unmanned aerial vehicles from the emergency network entity using the control link, where the emergency location was obtained from a gunshot detection system; control the unmanned aerial vehicle dispatch controller to deploy a first unmanned aerial vehicle to the emergency location specified by the emergency location data; and control the unmanned aerial vehicle dispatch controller to deploy the second unmanned aerial vehicle to a perimeter location within a predetermined distance from the emergency location.

A disclosed apparatus includes a processor operative to connect to at least one emergency network entity via an Internet connection, to provide an emergency event queue at the at least one emergency network entity; and an unmanned aerial vehicle dispatch controller, operatively coupled to the processor, and to an unmanned aerial vehicle radio controller. The unmanned aerial vehicle dispatch controller is operative to: establish an unmanned aerial vehicle control link between an unmanned aerial vehicle and the at least one emergency network entity via the Internet connection; deploy the unmanned aerial vehicle to an emergency event location for an emergency in the emergency queue; and provide data from the unmanned aerial vehicle on a display of the at least one emergency network entity. The unmanned aerial vehicle dispatch controller may be further operative to: provide a location indicator on the display of the at least one emergency network entity, on a map view showing the unmanned aerial vehicle location on a map view updated in real time.

Turning now to the drawings wherein like numerals represent like components, FIG. 1 illustrates an emergency data manager 100 which is operative to communicate with various emergency networks 170 including, but not limited to, multiple Enhanced 9-1-1 (E911) or Next Generation 9-1-1 (NG911) emergency networks 170, via network connections 175. The emergency data manager 100 is operatively coupled to a UAV (unmanned aerial vehicle) radio controller 200 by a connection 201 which may be an Internet connection in some embodiments. The UAV radio controller 200 is coupled to a UAV base station 203 via a backhaul connection 202. The UAV base station 203 provides wireless control links 204 to control a UAV fleet 205.

E911 and NG911 emergency networks are defined according to the National Emergency Number Association (NENA) standards which define applicable network architectures and protocols for communication between various network entities within the network architectures. Emergency networks are owned and operated by various emergency service providers (ESPs) such as, but not limited to, municipalities, state governments, and other public safety services (PSS) as well as private emergency service providers such as corporate security, college campus security, etc. The emergency services provided are for example, police, fire department, ambulance, etc. One type of emergency network is a public safety answering point (PSAP), which may handle emergency calls for police, fire and medical emergencies. Put another way, an ESP is an organization that owns and operates an emergency network where the emergency network includes the infrastructure, network entities, communication devices and other equipment required to provide the emergency services.

In FIG. 1, double arrowed lines represent operative coupling which may be implemented as backhaul connections between network entities, or as wireless connections between network entities and devices. Curved, dotted lines in FIG. 1 represent network connections or data connections over which data may be sent and received by respective devices, network entities or by combinations of devices and network entities sending data to, and receiving data from, each other, accordingly. The network connections may be Internet connections and may further include Virtual Private Network (VPN) pathways or other secure connections. The emergency data manager 100 is operatively coupled to emergency networks 170 via operative coupling 178, which may be implemented as network connections 175 through the Internet 190. The network connections 175 may include an Internet protocol (IP) connection between each of the emergency networks 170 and the emergency data manager 100 and may be connection oriented or connectionless. For example, the network connections 175 may include IP connections which may include a TCP (Transmission Control Protocol, also referred to as Transport Control Protocol) connection, a UDP (User Datagram Protocol) connection or a combination of both such as UDP over TCP, etc., or a combination of TCP and UDP connections, etc. An IP connection may further employ one or more TCP sockets or one or more WebSocket connections. The emergency networks may have backhaul connections 173 to the Internet 190 and backhaul connections 176 to national or regional emergency networks 180.

The emergency data manager 100 is also operatively coupled to various alarms 196 such as, but not limited to, burglar alarms, fire alarms, carbon monoxide alarms, water level alarms etc., and to various sensors 197 such as, but not limited to video cameras, motion detectors, audio sensors, glass break detectors, heat sensors, water level sensors, and automobile sensors such as airbag deployment sensors, collision sensors, gyroscopes and inertia detectors, etc. Some automobile sensors may be considered alarms. The various alarms 196 may be operatively coupled to screener networks 195 that receive the alarm data 198 outputs and perform alarm validation and scoring procedures. The screener networks 195 are operatively coupled to the emergency data manager 100 via an Internet connection. The various sensors 197 may also provide sensor data 199 to the emergency data manager 100 via the Internet using an appropriate connectivity networks such as wireless networks 110 or via some other means of Internet 190 connection.

The emergency data manager 100 may operate as an interface between the emergency networks 170, databases 120 and devices 160, to provide emergency data to the emergency networks 170. The emergency data manager 100 is operative to retrieve various types of emergency data such as location data, medical data, sensor data, camera data and other data, etc., determine the appropriate emergency network 170 authorized to receive specific emergency data, and provide that specific emergency data to the authorized emergency network. The emergency data manager 100 may, under some circumstances and for certain types of emergency data, store obtained emergency data in one or more databases which may be distributed databases. Protected data may be stored in protected data database 191 that may contain data that is subject to laws, regulations or policies that define how the data is accessed and handled. Among other things, the emergency data manager 100 is operative to obtain mobile device location data in response to a mobile device initiating an emergency call 103 or sending an emergency alert 105.

The emergency data manager 100 may communicate with, and retrieve and obtain data from, any of the various databases 120, any of which may contain protected data, and may also receive and store emergency data from the devices 160. The emergency data manager 100 is operative to determine the authorized emergency network using a geofence database 101 which includes boundary information for all of the emergency networks 170 and also for national or regional emergency networks 180.

The various emergency networks 170 may include various public safety answering points (PSAPs) which may answer emergency calls and accordingly dispatch police, fire departments and ambulances. Each emergency network such as, but not limited to a PSAP, may include an emergency dispatch center and employ a computer aided dispatch (CAD) system. Each emergency network 170 includes various emergency network entities such as at least one emergency network entity 140 which may be a PSAP workstation implementing a CAD system, a call handling system etc., and which provides various graphical user interfaces (GUIs) on a display 141 for use by emergency network personnel. The term "emergency network entity" refers to a hardware apparatus used to access or implement an emergency network such as, but not limited to, workstations, servers, routers, switches, laptops, desktop computers, etc. An emergency network entity hardware apparatus may include software or firmware related to its emergency network function.

Each individual emergency network 170 may include an emergency call handling system which is operatively coupled to a PSTN (public switched telephone network) and various wireless networks 110 via appropriate backhaul connections and call routing 171. The various emergency networks 170 are each operative to receive emergency calls 103 from a variety of devices 160 and a variety of device types. Each individual emergency network 170 may also receive emergency alerts 105 and establish emergency sessions 108 from the various devices 160 over the Internet 190. An emergency alert 105 may be sent as, for example, short message service (SMS) messages, SMS data messages, instant messages (IM), multi-media messages (MMS), email, or other formats of messages sent as Internet Protocol (IP) messages. For example, IP based messages may be sent using TCP, UDP, SIP, HTTP, or other mechanisms, etc. Emergency sessions 108 may also be established using these same, or other, IP protocols. An emergency session 108 refers to communication over an Internet connection between any the various types of devices 160 and an emergency network, where there is communication between one of the devices 160 and a particular emergency network of the emergency networks 170. The communication may be bi-directional. One example of a bi-directional emergency session 108 is a Voice-over-IP (VOIP) call using Session Initiation Protocol (SIP). Another example is an IP call using H.323 protocol, or some other communication protocol, etc. An emergency alert 105 may be, but is not limited to, data sent from a device 160 to a given one of the emergency networks 170. Because the emergency alert 105 will contain information that identifies the specific device 160 that sent the alert, the specific emergency network that received the emergency alert 105 may be able to respond to the device 160 by sending a response or acknowledgement message, or by making a call-back if the device 160 is for example, a mobile telephone such as a smartphone 107. The information that identifies a specific device 160 is referred to herein as a "device identifier." That is, a "device identifier" refers to information allowing identification of the device or a user of the device, such as for example, a phone number associated with a user, an email address, physical address, coordinates, IMEI number, IMSI, TMSI, IP address, BSSID, SSID or MAC address.

The various types of devices 160 that may communicate with an emergency network include, but are not limited to, desktop computers, laptop computers, tablets, mobile phones, smartphones 107, smartwatches 111 (or other health and medical tracking devices), medical bracelets 109, and various wired devices which may be Internet-of-Things (IoT) devices 113 which are operative to send and receive data from a wireless network such as, but not limited to, a 5th generation mobile network (5G network). A medical bracelet 109 may be a type of IoT device and may be operative to transmit an emergency alert 105 to an emergency network. Emergency calls may also be made from landline phones connected to a PSTN and medical bracelet 109 and/or health monitoring device, such as a medical bracelet 109, may use a wireless access point connected to the PSTN to place an emergency call 103 or send emergency alert 105. Some medical devices, which may be implanted in the human body or connected with the human body such as, but not limited to, a pacemaker, an insulin pump, etc., may also be operative to send emergency alerts 105.

An "emergency alert" refers to a communication relating to an emergency or non-emergency situation. That is, an emergency alert may be an emergency request for assistance where the emergency alert is associated with an emergency situation. An emergency alert may include information related to a device, the device user, past and current location, or an indication of the type of emergency such as, but not limited to, police, fire, medical, CO level, traffic accident or some other information in various combinations. An emergency alert may be associated with a non-emergency situation such as a request for a tow truck after a car breaks down. In other words, a situation that requires assistance, but is not necessarily a life-or-death critical situation. Emergency alerts may be associated with a device that sent the alert, or may be associated with a device not sending the alert such as a device making a proxy request on behalf of a second device or a member device in a group of devices, etc. An emergency alert may be "associated" with a device or user when the emergency alert relates to an emergency or non-emergency situation involving the device or user. Emergency alerts may include pointers to other sources of information such as, but not limited to, medical records and health data for the device user, or for another device user in a proxy situation, etc.

In one example of operation, an emergency alert 105 may be triggered by a device 160 in any of various ways such as, but not limited to, device fall detection, by the user pressing a soft button or a physical button (i.e. a "panic button"), a voice command, a gesture, or autonomously based on other sensor data such as via a smoke, carbon-monoxide, burglar alarm, or some other alarm, etc. In some situations, the user may confirm the emergency or provide authorization for sending the emergency alert 105.

Emergency data, such as enhanced location data, medical data, or other data, may be sent by the devices 160 to the various databases 120 and pushed to the emergency data manager 100 as part of the emergency alert 105. The emergency data may be sent from the devices 160 as updates 106 to a specific database of the various databases 120. The data updates 106 may be pushed to the emergency data manager 100 based on a subscription of a particular device 160 to the emergency data manager 100 services, or when a device 160 initiates an emergency session 108. In either case, the emergency data manager 100 may store the data in the protected data database 191 for a period of time in anticipation of an emergency data request from one of the emergency networks 170. The emergency data manager 100 is operative to provide emergency data in the protected data database 191, or access and provide emergency data in the databases 120 in response to an emergency data request. An emergency network 170 or an emergency responder device 150 may send an emergency data request to the emergency data manager 100.

Each of the devices 160 may be operative to send data updates 106 from time-to-time, or based on a schedule, to various databases 120 and this data may subsequently be used as information included in emergency alerts 105. The databases 120 may contain protected data in that the data is subject to various statutorily defined protections, such as, but not limited to, HIPPA, GDPR, or other statutorily defined data protection and data privacy requirements. The databases 120 may include location databases 121, medical databases 123 and other databases 125 with various personally identifiable data related to device 160 users. The data contained in the databases 120 is referred to as "emergency data" in that it may be retrieved by the emergency data manager 100, via an IP connection 161, in response to a detected emergency detected by the emergency data manager 100 or in response to an emergency data request.

Each emergency network 170 has at least one emergency network entity 140 which may be, for example, a workstation that includes one or more processors that are operative to execute one or more emergency services related applications, a display 141 and emergency response logic 144 in accordance with the various embodiments. In some embodiments, the emergency response logic 144 may be implemented as an application executed by the one or more processors of the emergency network entity 140. The emergency response logic 144 is operative to provide a graphical user interface (GUI) 143 on the workstation display 141. During operation, the emergency network entity 140 may also display other GUIs such as GUI 142, which may be related to, and provided by, other emergency response applications such as, but not limited to, an emergency call handling application or a computer aided dispatch (CAD) application.

The emergency response logic 144 is operative to communicate with the emergency data manager 100. The emergency data manager 100 may be included within an emergency data management network 102 which may include one or more servers, and one or more databases such as geofence database 101 and protected data database 191. The emergency data manager 100 may be implemented as a server having at least one processor, or may be implemented as a distributed system with multiple servers, processors, memory and databases, and may further provide cloud-based, software-as-a-service (SaaS) features and functions and/or may be implemented as SaaS using a platform-as-a-service (PaaS).

The GUI 143, in conjunction with the emergency response logic 144, are operative to retrieve and display emergency data provided by the emergency data manager 100 including, but not limited to, an emergency call queue and an alarm queue. More particularly, the GUI 143 provides communication between an emergency network entity such as the emergency network entity 140, and the emergency data manager 100. The GUI 143 may be implemented as a web browser interface, such as a cloud-based application interface (i.e. a software-as-a-service SaaS interface), or via a web browser plug-in, or may be associated with an application running as executable instructions, executed by one or more processors on the emergency network entity 140, or by any other software implementation mechanism. Emergency services personnel may receive appropriate emergency services information and view emergency data via the GUI 143.

Depending on the specific operations of the emergency network and the particular type of emergency network entity 140 software, the GUI 142 may be used by emergency services personnel to place dispatch calls to emergency responders, who receive the dispatch calls and emergency data on various emergency responder devices 150 accordingly. Emergency responders, also referred to as emergency service providers (ESPs) may utilize a variety of emergency responder devices 150 which may include, but are not limited to, desktop computers, laptop computers, tablets, mobile phones, smartphones, radios (i.e. walkie-talkies), in-vehicle computers, etc., all of which are operative to display emergency data to the emergency responders. The devices 150 may be operative to send emergency data requests 151 to a respective emergency network 170 and also authentication data 153. The devices 150 communicate with the emergency networks 170 over a combination of wireless networks 110 and proprietary wireless networks that provide wireless communications links 177. Each of the devices 150 may include a mobile emergency data application, that provides a GUI 155 and that is operative to communicate with the emergency response logic 144 and the emergency data manager 100. In response to emergency data requests 151, the emergency data manager 100 is operative to provide limited access to emergency data 157 to the emergency responder devices 150 based on the authorization level of the specific emergency responder device 150 and associated user.

An emergency data request 151 from an emergency responder device 150, may be sent either by a responder device 150, or by an appropriate one of the emergency networks 170, to the emergency data manager 100 such that the emergency data manager 100 may identify the emergency and any emergency data pertaining to the emergency stored by the emergency data manager 100 or contained within the various databases 120. In response, the emergency data manager 100, may check authorization, and then proceed to send the pertinent emergency data 157 to the requesting emergency responder device 150. In other words, in some implementations, the emergency data manager 100 may serve as a data pipeline for emergency responder devices 150 through which the emergency responder devices 150 may request and retrieve reliable emergency data through secure pathways using defined protocols and formats. The emergency data may be, but is not limited to: accurate location data, that is critical for responding to an emergency, medical data, sensor data, or other data, etc. The emergency data manager 100 is operative to obtain emergency data from various sources including other servers, databases 120, devices 160, alarms 196 and sensors 197.

In one example of operation, an emergency alert 105 may be triggered by a device 160 in any of various ways such as, but not limited to, device fall detection, by the user pressing a soft button or a physical button (i.e. a "panic button"), a voice command, a gesture, or autonomously based on alarm 196 data or sensor 197 data such via a smoke, carbon-monoxide, burglar alarm, or some other alarm, motion detector, camera, etc. In some situations, the user may confirm the emergency or provide authorization for sending the emergency alert 105. In one example, an alarm data 198 from a burglar of fire alarm may be sent to one of various screener networks 195. Screener network personnel may place a call to a keyholder and request further validation. If the alarm is validated by the keyholder, the screener network personnel may assign a priority score to the alarm and send it as a prioritized alarm to the emergency data manager 100. Some alarm data 198 that does not first pass through one of the screener networks 195 is received by the emergency data manager 100 as unprioritized alarm data. The emergency data manager 100 is operative to perform alarm verification and scoring procedures to determine whether the alarm data should be pushed to one of the emergency networks 170.

Emergency data, such as enhanced location data, medical data, or other data, may be sent by a device 160 to an appropriate one of the emergency networks 170 as part of an emergency alert 105, or may be sent as data updates 106 to a specific database of the various databases 120. In some implementations, and/or for certain types of emergency data, the emergency data manager 100 may push emergency data to a given emergency network 170 as that emergency data is obtained by the emergency data manager 100. An emergency network 170 may also, at any time, send an emergency data request to the emergency data manager 100 such that the emergency data manager 100 may search or query the various databases 120. In some implementations, an emergency data search may be performed by the emergency data manager 100, using the IP connections 161 to the various databases 120, in response to an emergency alert 105, emergency call 103, or emergency session 108 between a device 160 and one of the emergency networks 170. In one example, the emergency data manager 100 is operative to receive Android™ Emergency Location Service (ELS) or Advance Mobile Location (AML) data upon initiation of an emergency call 103, emergency alert 105, or emergency session 108 by a device 160 that utilizes the Android™ operating system. Upon receipt of ELS or AML data, the emergency data manager 100 is operative to push the ELS or AML data to the appropriate emergency network 170 based on a geofence analysis using the geofence database 101. The emergency data manager 100 may also perform a search of the various databases 120 using a device identifier in the ELS or AML data to identify additional related emergency data and push that emergency data to the appropriate emergency network 170.

The emergency data manager 100 or the emergency network 170 may format stored emergency data or any received emergency data into a format that is compatible with industry standards for storing and sharing emergency data. For example, the emergency data may be formatted to be compatible with National Emergency Number Association (NENA) standards. Where emergency data is stored by the emergency data manager 100, emergency data requests may be sent to the emergency data manager 100 by an emergency network, such as via an HTTP GET request. For example, protected data may be stored in the protected data database 191 pending receipt of appropriate authorization credential by the emergency data manager 100. In other words, some emergency data may be pushed to emergency networks 170 upon receipt by the emergency data manager 100, while other data, if subject to the categorization of protected data, may only be sent upon receipt of proper authorization and/or in conjunction with an authorized emergency data request.

Emergency data requests 151, whether sent directly by a responder device 150 or via an emergency network 170 may utilize Location Information Server (LIS) protocol. For emergency data related to location, the data may include, but is not limited to, device generated location data (such as device 160 GPS chipset data), location information such as Location-by-Reference, Location-by-Value, etc. from, for example a, Location Information Server (LIS) or from other sources. Such location data that contains multiple location determination method data is referred to as hybrid location data.

Each of the emergency networks 170 may be operatively coupled, via appropriate backhaul connections 176, to one or more national or regional emergency networks 180. The national or regional networks 180 each include an emergency event application 181 which is operative to, among other things, display emergency events for a hierarchical view of emergencies being handled by one or more of the emergency networks 170.

Figure 2:
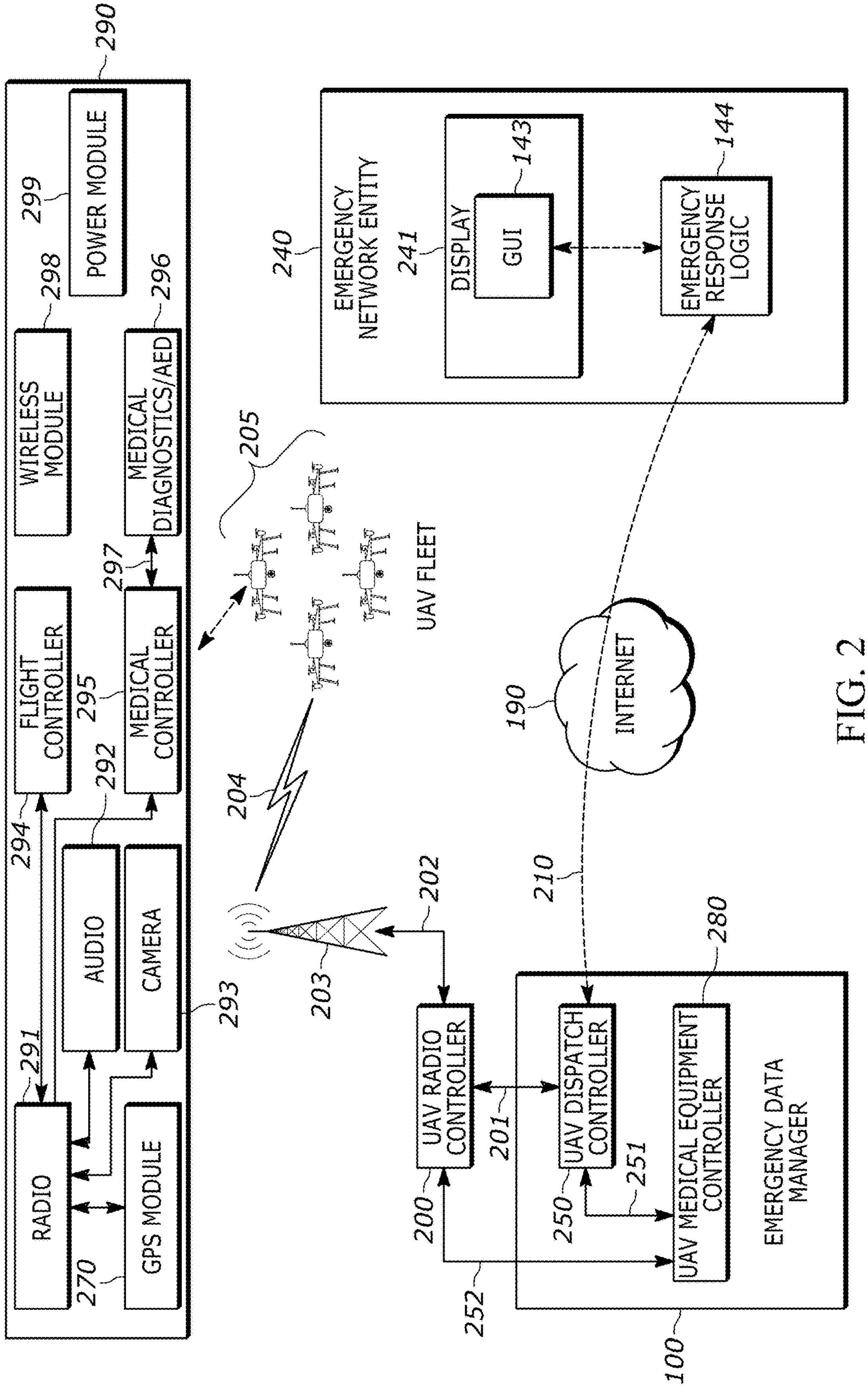
FIG. 2 is a block diagram of showing further details of an emergency data manager having a UAV dispatch controller to control a UAV fleet in accordance with various embodiments.

FIG. 2 provides further details of the emergency data manager 100, which includes a UAV dispatch controller 250 and a UAV medical equipment controller 280. The UAV dispatch controller is operatively coupled via a connection 251 to a UAV medical equipment controller 280 to receive data and send control commands to a medical payload 296 on a UAV. The emergency data manager 100, the UAV dispatch controller 250 and the UAV medical equipment controller are apparatuses in accordance with the present disclosure. The emergency data manager 100, the UAV dispatch controller 250 and the UAV medical equipment controller 280 are operatively coupled, via an Internet connection 210, to emergency response logic 144, which is within an emergency network entity 240 of an emergency network 170. The emergency data manager 100, the UAV dispatch controller 250 and the UAV medical equipment controller 280 are operatively coupled to multiple emergency network entities of multiple emergency networks 170.

An example UAV 290 includes radio equipment 291 which includes a transceiver and various antennas, audio equipment 292 which includes one or more microphones such as a microphone array, and a speaker, a camera 293 and a GPS module 270. The radio equipment 291 is operatively coupled to a flight controller 294 which is programmable, and a medical controller 295 which is also programmable. The camera 293 is operative to provide a video feed from the UAV and the GPS module 270 is operative to track the UAV 290 position. A power module 299 provides one or more rechargeable battery packs to power the UAV 290. A wireless module 298 provides additional wireless capabilities for communicating with a medical diagnostics payload 296, such as via Bluetooth™, to ad hoc network with other UAVs in the fleet, or to provide radio triangulation capabilities, etc.

The UAV dispatch controller 250 establishes a UAV control link to the UAV fleet through the UAV radio controller 200, the UAV base station 203 and wireless control links 204. The UAV medical equipment control 280 may share the UAV control link to communicate with the medical diagnostics payload 296. The emergency response logic 144, on an emergency network entity 240, may assume control of the UAV fleet 205 via the Internet connection 210 and using the graphical user interface 143 on an emergency network entity display 241.

Figure 3:
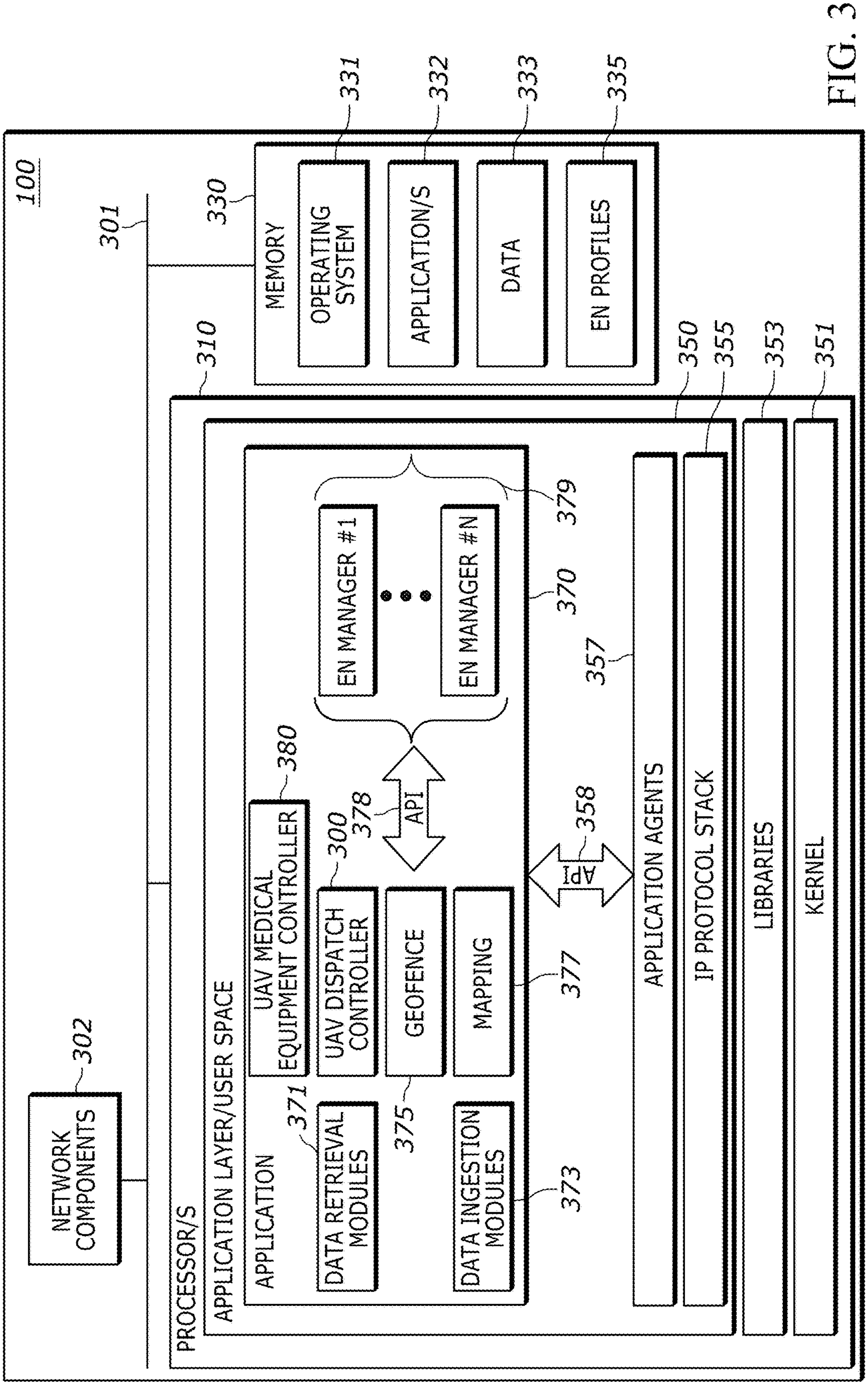
FIG. 3 is a diagram providing further details of an emergency data manager in accordance with one embodiment.

FIG. 3 provides an example implementation of the emergency data manager 100 which is an apparatus shown in FIG. 1 and FIG. 2. The emergency data manager 100 includes network components 302, at least one processor 310, and at least one non-volatile, non-transitory memory 330 in addition to RAM (random access memory). The at least one processor 310 is an emergency data management processor and is another type of apparatus disclosed herein. The network components 302 may include one or more network transceivers for Ethernet connectivity to other network entities and an Internet connection. The memory 330 stores executable instructions and data such as operating system 331 executable instructions and various application executable instructions 332. The operating system 331 executable instructions and the application executable instructions 332 may be executed by the at least one processor 310. The memory 330 also stores data 333 which may provide a location and geofence data cache, other data caches and other data, etc., and emergency network profiles 335 which provide login credentials, settings and other data related to emergency networks that access the emergency data manager 100.

The processor 310 may be implemented as one or more microprocessors, ASICs, FPGAs, microcomputers, microcontrollers, digital signal processors, central processing units, state machines, logic circuitries, and/or devices that manipulate signals based on operational instructions. Among other capabilities, the processor 310 is configured and operative to fetch and execute computer-readable instructions (i.e. executable instructions) stored in the memory 330. For example, the operating system 331 executable instructions, when executed by the at least one processor 310, may provide a kernel 351, libraries 353 (i.e. application programming interfaces or "APIs"), an application layer 350 or "user space" within which the various applications are executed, and an IP protocol stack 355. The applications executable instructions 332, when executed by the at least one processor 310, also provide UAV dispatch controller 300, UAV medical equipment controller 380, data retrieval modules 371, data ingestion modules 373, a geofence module 375, a mapping module 377, and one or more emergency network managers 379. Emergency network profiles 335, stored in memory 330, may be accessed by the various modules and the emergency network managers 379 to access information needed to communicate with various emergency networks.

The emergency network managers 379 communicate with the other modules of application 370 via a set of APIs 378 and coordinate communication between emergency network entities and the UAV dispatch controller 300 and UAV medical equipment controller 380. The emergency network managers 379 monitor emergency queues on each emergency network entity and may control the UAV dispatch controller 300 to automatically dispatch UAVs to an emergency location. The emergency network managers 379 track the locations of the UAV fleet 205 and operating conditions such as available battery power, etc. The emergency network managers 379 maintain an awareness of the estimated time-of-arrival (ETA) for each UAV to respective emergencies based on emergency location data that is received via the data ingestion modules 373. Therefore, UAV availability is determined using UAV status, UAV capability such as whether a given UAV has a required medical diagnostics payload, and the UAV ETA for a given emergency location.

The processor 310 may further execute a set of application agents 357 which facilitate communication between the IP protocol stack 355 and the application 370 via various APIs 358. The application agents 357 are operative to, among other things, provide API communication between the various applications and the kernel 351.

In accordance with an embodiment, the UAV dispatch controller 300 and/or UAV medical equipment controller 380 may be implemented as applications executed by the at least one processor 310. In some embodiments, the UAV dispatch controller 300 and/or UAV medical equipment controller 380 may be implemented using ASICs, FPGAs, DSPs, or combinations thereof. In one example embodiment, the UAV dispatch controller 300 and the UAV medical equipment controller 380 may be implemented together as an integrated ASIC that is operatively coupled to the at least one processor 310, or each as a separate ASIC operatively coupled to the at least one processor 310.

The emergency data manager 100 may be implemented as a cloud server. The term "cloud server" as used herein, refers to a server, accessible by an Internet connection, that is operative to host one or more applications that may be accessed by a computing device using a Web browser or an application resident on the computing device. The emergency data manager 100 is operative to provide a cloud-based application such as a software-as-a-service (SaaS) accessible remotely using a computer or workstation connected to the Internet and operatively coupled to the emergency data manager 100. The emergency data manager 100 may be implemented as SaaS software executed using a platform-as-a-service (PaaS) that enables development and execution of cloud-based applications.

All of the components of the emergency data manager 100 are operatively coupled by an internal communication bus 301. As used herein, components may be "operatively coupled" when information can be sent between two such components, even though there may be one or more intermediate or intervening components between, or along the connection path. Therefore, any of the various components with the emergency data manager 100, and in other example network entities and devices described herein, may be understood herein to be operatively coupled to each other where appropriate, and to be executing on one or more processors that are further operatively coupled to a memory that stores executable instructions (also referred to as "software code" or "code") for implementing the various components. Operative coupling may also exist between engines, system interfaces or components implemented as software or firmware executing on a processor and such "software coupling" may be implemented using libraries (i.e. application programming interfaces (APIs)) or other software interfacing techniques as appropriate. Such libraries or APIs provide operative coupling between various software implemented components of FIG. 3. A "module" as used herein may be a software component. That is, the UAV dispatch controller 300, UAV medical equipment controller 380, data retrieval modules 371, data ingestion modules 373, geofence module 375, mapping module 377, and one or more emergency network managers 379 are all operatively coupled to each other via APIs 378 and are operatively coupled to the IP protocol stack 355 and to the application agents 357 via APIs 358.

All of the components and modules described herein may be implemented as software or firmware (or as a combination of software and firmware) executing on one or more processors, and may also include, or may be implemented independently, using hardware such as, but not limited to, ASICs (application specific integrated circuits), DSPs (digital signal processors), hardwired circuitry (logic circuitry), or combinations thereof. That is, any of the components or modules disclosed herein may be implemented using an ASIC, DSP, FPGA executable instructions executing on a processor, logic circuitry, or combinations thereof. In other words, the components and modules may be implemented as hardware, software or by combinations thereof. Therefore, each of the components and modules disclosed herein may be considered a type of apparatus that may be implemented and operate independently from the other components in the system. For example, any one of the data retrieval modules 371, data ingestion modules 373, geofence module 375, mapping module 377, UAV dispatch controller 300, UAV medical equipment controller 380, or emergency network managers 379 may be implemented using an ASIC, DSP, FPGA, executable instructions executing on a processor, logic circuitry, or combinations thereof. In one example embodiment, the UAV dispatch controller 300, UAV medical equipment controller 380, geofence module 375 and mapping module 377 may be implemented together as a single ASIC that is operatively coupled to the at least one processor 310.

The various embodiments also include computer readable memory that may contain executable instructions, for execution by at least one processor, that when executed, cause the at least one processor to operate in accordance with the emergency data manager 100 and other functionality herein described. The computer readable memory may be any suitable non-volatile, non-transitory, memory such as, but not limited to, programmable chips such as EEPROMS, flash ROM (thumb drives), compact discs (CDs) digital video disks (DVDs), optical drives, etc., that may be used to load executable instructions or program code to other processing devices or electronic devices such as those that may benefit from the features and methods of operation herein described. The executable instructions may also include the various operating system environments and the kernel. For example, the memory 330, which is a non-volatile, non-transitory memory, may store executable instructions for execution by the at least one processor 310 that when executed, provide the data retrieval modules 371, data ingestion modules 373, geofence module 375, mapping module 377, UAV dispatch controller 300, UAV medical equipment controller 380, or emergency network managers 379.

The emergency data manager 100 is operatively coupled to a geofence database 101 which stores jurisdictional boundary data for various emergency networks 170 as well as for the national or regional emergency networks. The geofence module 375 is operative to access the geofence database 101 and determine which emergency network 170 should receive specific emergency data obtained by the data ingestion modules 373, based on analysis of the geofences specified in the geofence database 101. The emergency data manager 100 is operative to store and retrieve emergency data from the various databases 120, and may function as an interface between emergency networks, the various databases 120 and devices 160 to receive and store emergency data. The stored emergency data can be transmitted or distributed to emergency networks and emergency responder devices 150 before, during, or after emergencies. The emergency data manager 100 is operatively coupled to a protected data database 191 which stores protected data related to emergencies. Protected data is either not stored by the emergency data manager 100 or is stored only for a predetermined period of time as defined by laws, regulations or policies, in the protected data database 191. The emergency data manager 100 may receive emergency data from any of the devices 160 and such data may include, but is not limited to, locations, medical history, personal information, or contact information. The emergency data manager 100 may receive emergency data from any of the devices 160 and such data may include, but is not limited to, locations, medical history, personal information, or contact information. The emergency network managers 379 are operative to check emergency network credentials to determine authorization and access levels to protected data stored in the protected data database 191 or in the other databases 120.

The emergency data manager 100 includes data ingestion modules 373 and data retrieval modules 371. The data ingestion modules 373 are operative to communicate with the various databases 120 and with the various alarms 196 and sensors 197 to obtain emergency data and may include a location ingestion module, an additional data ingestion module, and one or more multimedia ingestion modules. The location ingestion module is an emergency location service ingestion interface which is operative to post or receive emergency locations. The location ingestion module may be a REST API that is operative to receive an HTTP POST including location data when an emergency alert 105 is generated or when an emergency call 103 is received from a device 160. The location data may include a location generated concurrently or in response to the generation of the emergency alert 105, which may initiate an emergency call 103 or emergency session for requesting emergency assistance. This generated location data may be, for example, location data from a device 160 GPS chipset, such as GPS coordinates. This data may also include data from a device 160 inertial-measurement-unit (IMU). The location data may be generated before an emergency alert 105 such as, for example, when a medical bracelet IMU detects that a patient has fallen. In another example, when an emergency call 103 is made from a device 160, the location ingestion module of the data ingestion modules 373 may receive a location recently generated by the device 160 GPS chipset, or by a device 160 triangulation algorithm, or other device 160 location mechanism, thereby ensuring that a location for the emergency is available as quickly as possible. The location data may include a device-based hybrid location generated by a device 160 which has sent an emergency alert 105. A GPS chipset within the device 160 may generate the location data. The location data may also include a location data generated by a second device 160 that is communicatively coupled to the device 160 that sent the emergency alert 105. For example, a wearable device such as a medical bracelet or smartwatch, that does not include location capabilities, may use the location services location from a mobile phone with which it is paired. The location ingestion module of the data ingestion modules 373 may communicate with a device 160 via a mobile application installed on the device 160 or via firmware or an operating system of the device 160.

The location data generated by a device 160 prior to an emergency occurrence may be accessible by an authorized one (based on device 160 location) of the emergency networks 170 during an emergency. For example, a taxi company may have software that transmits the location of its cars or assets to the emergency data manager 100, or another server, preemptively. Thus, when an emergency arises, the location of the affected taxi can be made accessible quickly to send for help. Further, location data generated by a device 160 after an emergency has commenced may be made accessible to one of the emergency networks 170 during the on-going emergency. For example, updated location data of a hijacked taxi may be periodically transmitted to the emergency data manager 100 and made accessible to one or more of the emergency networks 170.

The data ingestion modules 373 may also provide an interface for posting or receiving static or dynamic emergency profile data. Such additional data may include, but is not limited to, medical data, personal data, demographic data, and health data, which may be obtained from the various databases 120. For example, medical data may include information relating to a person's medical history, such as medications the person is currently taking, past surgeries or preexisting conditions. Personal data may include a person's name, date of birth, height, weight, occupation, addresses such as home address and work address, spoken languages, etc. Demographic data may include a person's gender, ethnicity, age, etc. Health data may include information such as a person's blood type or biometrics such as heart rate, blood pressure or temperature. Additional data may further include data received from connected devices such as vehicles, IoT devices 113, and wearable devices such as medical bracelet 109, smartwatch 111 or other devices, alarms 196 and sensors 197, etc. Each of the sensors 197 may be IoT devices. Some sensors may be clustered and connected to a centralized sensor hub that is operative to connect to the Internet 190 and communicate with the emergency data manager 100 via the data ingestion modules 373.

The data ingestion modules 373 are operative to receive data from alarms 196 and from sensors 197. Some alarms 196 may also be accompanied by, or integrated with, various sensors. For example, intelligent vehicle systems may generate and send sensor data regarding a crash, such as the speed at which the vehicle was moving just before the collision, where the vehicle was struck, the number of occupants, etc. as part of, or along with, a collision alarm indication. The data ingestion modules 373 may be implemented in whole or in part using a REST API, for example using JSON (JavaScript Object Notation).

In one example of operation, if an emergency call 103 is made from a mobile phone, or if an emergency alert 105 is sent, the mobile phone may receive a heart rate of the person who made the emergency call from a smartwatch 111 worn by the person and communicatively coupled to the cell phone via a Wi-Fi™ or Bluetooth™ connection or some other wireless connection. The mobile phone may therefore send the heart rate to the data ingestion modules 373, along with any other additional data, in an HTTP POST. The data ingestion modules 373 may communicate with a device 160 via a mobile application installed on the device 160 or integrated into the firmware or operating system of the device 160. Additional data may also be sent to the data ingestion modules 373 from a network server. The data ingestion modules 373 may be accessed by any connected platform that receives data that might be relevant in an emergency. Connected platforms, such as the various databases 120, may therefore send additional data to the data ingestion modules 373 at any time. A website, web application, or mobile application may communicate with the data ingestion modules 373 and may allow device 160 users to create profiles to send additional data included in the profiles to the data ingestion modules 373 every time a profile is created or updated. Profiles may also be created for each of the alarms 196 and sensors 197 such that the data ingestion modules 373 receive additional data in addition to alarm data, such as a keyholder's phone number or other contact information, medical information, or other information contained in the profile, etc.

The data ingestion modules 373 may also include a multimedia ingestion module to provide an interface for posting or receiving data such as audio or video streams obtained during an emergency from a device 160 or sensor 197 that is proximal to the emergency, for example data may be received from a video camera operating as a sensor 197 or from some other type of sensor such as a gunshot detection system. The data ingestion modules 373 may also receive data from the UAV fleet 205 including, but not limited to, medical diagnostics payload data, location data, audio data, video data, image data, or other data, etc. In one example of operation, if an emergency alert 105 is generated by an intelligent vehicle system installed in a vehicle in response to the vehicle experiencing a collision, the emergency alert 105 is sent to one of the emergency networks 170 by the intelligent vehicle system or by another device 160 communicatively coupled to the intelligent vehicle system, such as a mobile phone coupled to the intelligent vehicle system via Bluetooth™. In response to generating the emergency alert 105, the intelligent vehicle system, or a proximal camera serving as a sensor 197, or a UAV camera 293, may additionally begin streaming audio and video from microphones and cameras. The intelligent vehicle system may include cameras installed inside or outside of the vehicle. The streaming audio and video are streamed to the emergency data manager 100 through the data ingestion modules 373. A mobile phone communicatively coupled to the intelligent vehicle system may additionally or alternatively stream audio or video from microphones and cameras integrated into the mobile phone to the emergency data manager 100 through the data ingestion modules 373. One or more multimedia ingestion modules of the data ingestion modules 373 may be implemented wholly or partly using REST APIs that are accessed with an HTTP POST. Audio or video may also be collected in response to the data ingestion modules 373 receiving data from one of the alarms 196.

After receiving the relevant data, the data ingestion modules 373 can store the data in one or more databases operatively coupled to the emergency data manager 100, such as the protected data database 191. The emergency data manager 100 may be operatively coupled to databases such as, but not limited to, a location database, the geofence database 101, the protected data database 191 etc. The emergency data manager 100 databases may also be operatively coupled to, or otherwise accessible by, one of the emergency networks 170. The data ingestion modules 373 are operative to tag or otherwise associate received data with an identifier of a user or specific device 160 associated with the data. For example, the data ingestion modules 373 may tag received data with a user ID number, an email address, or a phone number (i.e. caller ID), a MAC address, an alarm ID, a sensor ID, or other device or user identification information, etc. The data ingestion modules 373 may also tag received data based on the data source using, for example, a device name or type, an application name, user name, phone number, corporate account, or etc. All data received by the data ingestion modules 373 is also analyzed by the geofence module 375 to determine which emergency network 170 should receive the data. Alarm 196 data is also analyzed by the false alarm detection logic 200 to determine an alarm scoring and determine whether the alarm is a false alarm or not, prior to pushing alarm data to an emergency network entity.

An individual or group of individuals may be associated with multiple identifiers. In an example of operation, if the data ingestion modules 373 receive a location generated by a phone associated with the phone number+1-555-555-5555, associated with John Doe, the data ingestion modules 373 may also receive a heart rate from a smartwatch associated with the email address jobndoe@email.com, which is an identifier that is also associated with John Doe. In this example, the data ingestion modules 373 tag the location with the phone number "+1-555-555-5555," and tag the heart rate with the email address "johndoe@email.com," thereby associating both the location and the heart rate with John Doe in the emergency data manager 100 databases. An alarm ID corresponding to one of the alarms 196 may also be associated with a phone number and email address associated with an individual or group of individuals.

Ingestion data that enters the emergency data manager 100 may include various data fields and associated data entries within the data fields. The emergency data manager 100 maintains a list of expected data fields so that the data entries can be entered within a specific data field.

The emergency data manager 100 may include data retrieval modules 371 such as a location retrieval module, an additional data retrieval module, and one or more multimedia retrieval modules. For example, a location retrieval module may provide an interface for retrieving location data from the emergency data manager 100 databases. The location retrieval module may be implemented wholly or partly via a JSON REST API that is operative to receive a query or request such as, but not limited to, an HTTP GET request, from the emergency networks 170 or an emergency responder device 150.

The data retrieval modules 371 may provide a single GET endpoint for retrieving either the latest or paginated list of locations for a specific caller ID, and/or associated protected data from the protected data database 191. For example, a phone number associated with a device 160 from which a location was received may be included in a header, body, or metadata of a request sent to the data retrieval modules 371. The emergency data manager 100 may then retrieve a location or set of locations from the emergency data manager 100 databases and deliver the location or set of locations to the relevant authorized emergency network 170 or to an emergency responder device 150 associated with the authorized emergency network. The location retrieval module of the data retrieval modules 371 may be a location information server (LIS), in which the LIS may further be a NG911 standards-based XML API for the retrieval of location data from the emergency data manager 100 databases. The location retrieval module of the data retrieval modules 371 may be operative to accept HELD requests from the emergency networks 170 or from emergency responder devices 150 and to return location data for a specific caller ID or anonymous reference.

The data retrieval modules 371 may also include an additional data retrieval module implemented as a JSON REST API for the retrieval of emergency or additional data. Additional data may include, but is not limited to, medical data, personal data, demographic data, health data or other data which may be protected data. Additional data may also include data received from connected devices 160 such as, but not limited to, vehicles, IoT devices, and wearable devices, alarms 196 and sensors 197. The additional data retrieval module of the data retrieval modules 371 may be operative to receive a query or request, such as an HTTP GET request, from an emergency network 170 or emergency responder devices 150. The additional data retrieval module of the data retrieval modules 371 may then, in response to a request, retrieve additional data associated with a specific or particular identifier of a user or a device 160 associated with the user, such as a phone number, and return the data to the emergency network 170 or emergency responder device 150. The data retrieval modules 371 may further include one or more multimedia retrieval modules, which function similarly to the location retrieval module and additional data retrieval module, for the retrieval of data stored in the emergency data manager 100 databases not retrieved by the location retrieval module or additional data retrieval module such as multimedia streaming data.

The emergency data manager 100 determines which of the emergency networks 170 and associated emergency responder devices 150 have authorization to receive particular types of emergency data. The emergency network managers 379 are operative to access emergency network profiles 335 and determine access levels to emergency data for emergency network entities and personnel. For example, a given emergency network 170 or emergency responder device 150 may, in certain circumstances, be granted access only to a particular subset of emergency data. For example, a police officer may only be given access to the location emergency data, while an EMT (emergency medical technician) may only be given access to an additional data emergency data. However, a given emergency network such as a national or regional emergency network, or associated emergency responder device 150, may be given differential access to the entirety of the emergency data, or to particular emergency data categories within the databases based on any factor or set of factors. A management portal may be provided by the emergency network managers 379 to determine which emergency data categories are returned from one of the emergency networks 170 to a particular emergency network 170 or emergency responder device 150. Other data services corresponding to the various databases 120 may also be coordinated with respect to granting access to protected data.

During an emergency, the emergency data manager 100 is operative to detect the emergency and/or otherwise identify the need to provide emergency data pertaining to the emergency. In response to detecting an emergency, the emergency data manager 100 is operative to identify any emergency data pertaining to the emergency stored within the databases 120 and protected data database 191, and retrieve and transmit the pertinent emergency data to the appropriate emergency network 170. The emergency data manager 100 may act as a data pipeline that automatically pushes emergency data to emergency networks that would otherwise be without access to emergency data that is critical to most effectively and efficiently respond to an emergency. Location data stored within, and/or obtained and provided by, the emergency data manager 100, enables emergency responders to arrive at the scene of an emergency faster, and the additional emergency data stored within, and/or obtained and provided by, the emergency data manager 100 enables emergency responders to be better prepared for the emergencies they face.

The emergency data manager 100 is operative to provide a cloud-based application to multiple emergency networks 170 by establishing network connections via the IP protocol stack 355, with various emergency network entities such as a call handling workstation, CAD workstation etc. Other examples of emergency network entities include, but are not limited to, servers, desktop computers, laptops, routers, switches, etc. that are operative to send and receive data. The network connections may be transport control protocol (TCP) connections and may utilize WebSocket connections between the emergency data manager 100 and an emergency network entity. The geofence module 375 is operative to determine emergency network jurisdictional boundaries and to show the jurisdictional boundaries on a graphical user interface as a jurisdictional map view. The mapping module 377 is operative to generate the jurisdictional map view and to also post emergency data locations as location indicators on the map. For example, location indicators may show the location of incoming emergency calls that the emergency network has received, or is receiving, as well as any incoming alarms and alerts. The emergency network managers 379 provide authentication and login capabilities for the various emergency networks and enable APIs 378 for communication between the emergency network entities and the data ingestion modules 373, data retrieval modules 371, UAV dispatch controller 300, UAV medical equipment controller 380, geofence module 375, and mapping module 377. For example, only qualified UAV operators may be allowed to control dispatched UAVs from their respective emergency network entity.

Emergency networks 170 and their corresponding emergency network entities are associated with a given geographic boundary. Based on the geographic boundary for a respective emergency network 170, a jurisdictional map view customized for the respective emergency network 170 may be generated and provided to emergency network entities 140, such as workstations, for display. Within the jurisdictional map view for a given emergency network 170, location indicators for emergencies occurring within its geographic boundary may be displayed. The jurisdictional map view for a given emergency network 170 may include one or more geofences associated with the respective emergency network 170 and surrounding areas. For emergency data received by the emergency data manager 100, the emergency data manager 100 may perform a geospatial query of all devices with a given geographic boundary using the geofence module 375, to search for additional emergency data related to the received emergency data and to obtain data from those devices such as sensors 197.

The geofence module 375 is operative for managing geofence data for emergency networks 170 including assigning geofences to one or more emergency responder devices 150 or emergency network members, etc. The emergency data manager 100, via the geofence module 375, is operative to filter all incoming emergency data related to devices 160, alarms 196 and sensors 197 by geofences. Emergency networks 170 utilize geofences that define jurisdictional boundaries within which a specific emergency network is authorized to respond to emergencies. For example, a city police department may have jurisdictional authority over the entire city, or of only a portion of the city. A geofence would represent the perimeter of the portion of the city that the respective police department serves. A geofence may therefore be considered a representation of a virtual perimeter overlaying a real-world geographic area.

Geofences may be used to define a county boundary, a state boundary, a collection of postal/zip codes, a collection of cell sectors, or etc. A geofence may be defined using simple shapes such as rectangle, triangle, circle, etc., or may be defined using complex polygons, etc. Geofences may also refer to approximations where the "approximated" geofence encloses an approximation of a jurisdictional boundary or some other boundary and may also include buffer regions extending outside the perimeter, for example one-mile or such beyond the primary geofence perimeter.

Some geofences can be dynamically generated by the emergency data manager 100. For example, a dynamic geofence may be generated as a radius around a point location at which an emergency is occurring. In another example, a geofence may be represent non-emergency network boundaries such as school zones or neighborhood boundaries, etc. The use of a geofence is referred to as geofencing. One example of geofencing involves a location-aware device or a location-based service (LBS) monitoring when the device enters or exits a given geofence. This means that the device is monitored within the geographic boundaries defined by the given geofence. Entry or exit from given geofence by the device may trigger an alert to the device's user as well as messaging a given network monitoring the geofence. The monitoring network may be an emergency network 170 but could be other types of networks as well. The geofence information may contain the device location, which could be sent to a mobile telephone, an email account or to some other system or network entity.

In the context of emergency services, one or more geofences may correspond to the jurisdictional boundaries of an emergency network 170. The emergency network 170 may be operated by a public entity and may be for example, a public safety answering point (PSAP), a police department, a fire department, a federal disaster management agency, national highway police, etc., which have jurisdiction over a designated area and, sometimes, overlapping areas. Geofences are used to define the jurisdictional boundaries using various Geographic Information System (GIS) formats. A GIS file format refers to one or more standards for encoding geographical information into a computer file.

For maintaining the privacy, security and integrity of emergency data, geofencing is applied to ensure that emergency data flows only the emergency network 170 having authority to access the information and responds to the given emergency. Applying geofence filters to the emergency data also allows additional avenues for monitoring, both visibility and control, over the emergency data manager 100 to detect anomalies or spikes and to reduce the risk of security breaches. The geofence module 375 monitors all accesses to emergency data, both incoming and outgoing from the emergency data manager 100 and is operative to filter emergency data to the appropriate authorized emergency network 170 or emergency responder device 150.

In an example of emergency data manager 100 operation, an emergency alert may be triggered by a given device 160, for example by fall detection, by a user pressing a soft button, a physical button, initiating a voice command, or gesture, or autonomously based on sensor data such as from a smoke detector. In this example, the user may be prompted to confirm the emergency or otherwise provide authorization for sending the emergency alert. However, for a fall detection scenario, a confirmation would not be required because the patient may be incapacitated. Emergency data, such as an enhanced location and additional data regarding the user, such as the user's medical history, may then be delivered by the device 160 to the emergency data manager 100 and stored in a database such as protected data database 191. The emergency data manager 100 may format the emergency data into a format that is compatible with industry standards for storing and sharing emergency data. For example, the emergency data may be formatted to be compatible with National Emergency Number Association (NENA) standards. The emergency data manager 100 may then perform a push operation to push the emergency data to an authorized emergency network entity. After the push operation, the emergency data manager 100 may delete any temporarily stored data if required for compliance with privacy laws, regulations and policies. For medical data, the emergency data manager 100 may push a candidate profile that provides basic information to be used by emergency network 170 personnel to identify a patient. Once the emergency network 170 personnel select the candidate profile on their GUI 143, the protected data for which they are authorized to receive will be pushed to their emergency network entity 140. Likewise, emergency personnel in the field may receive the protected data using an emergency data application and via a GUI 155 on an emergency responder device 150.

Alternatively, or in addition to push operations, emergency data may also be obtained by the emergency networks 170, such as by a PSAP responding to an emergency alert, by sending a query to the emergency data manager 100. The query may be an emergency data request using, for example, an HTTP GET request. The emergency data request may also be in the form required by the Location Information Server (LIS) protocol. In response to the emergency data request, the emergency data manager 100 sends an appropriate response including relevant emergency data to the requesting party via an encrypted pathway. The emergency data request may be in the form of an HTTP-Enabled Location Delivery (HELD) and the response from the emergency data manager 100 may be in the form of a Presence Information Data Format Location Object (PIDF-LO) as defined by the Internet Engineering Task Force (IETF).

The emergency data request includes an authorization code, also referred to as an "authorization token", in the body, header, or metadata of the request, and the emergency data manager 100 checks that the authorization code is active before providing a response to the requesting party. Authorization may be provided in the "Authorization" header of the emergency data request using HTTP Basic Authentication. For example, authorization may be a base64-encoded user name and password for an account associated with the requesting party. Emergency data requests are sent over public networks using API access keys or credentials. Transport Layer Security (TLS) may be used in the requests and responses from the emergency data manager 100 for encryption security. In some implementations, the API access keys or credentials are sent using Extensible Markup Language (XML) in a message header and may be further encrypted for additional security. If an emergency data request includes an inactive or expired credential or access key, an error response may be generated and sent to the requesting entity by the emergency data manager 100. The emergency network managers 379 are operative to verify the access keys or credentials and enable the data retrieval modules 371 to respond to verified authorized emergency data requests by sending the pertinent emergency data.

Emergency data may include locations and additional data such as protected data. Emergency data may include one or more emergency data categories, also referred to as "data categories". The emergency data categories may include, for example: service data reference, full name, email, emergency contacts, addresses, language, occupation, phone numbers, websites, gender, height, weight, ethnicity, profile picture, allergies, medical conditions, medications, disabilities, blood type, medical notes, birthday, and additional comments. Emergency data categories may be tagged with tags for specific types of data such as "demographics" or "medical data." For example, gender, height, weight, ethnicity, profile picture (image-url) may be tagged as demographic data. Medical data protected under HIPAA and other laws may be tagged as "HIPAA" or "private." Medical data may include information on one or more of allergies, medical conditions or illnesses, medications, disabilities, blood type, medical notes, and other medical information. Medical information protected under HIPAA are encrypted and/or anonymized. Some data are tagged as "general" or another similar tag, wherein access is not specifically restricted.

The emergency data manager 100 may store emergency data requested by an emergency network entity 140 in a remote database, such as the protected data database 191, for a certain period of time after receiving the request for the emergency data regarding a user and any electronic devices 160. A purge period of time may be set as a timer value, such as a timer countdown or a set time point, which may be defined by the emergency network that sent the emergency data request. An emergency data purge period may be, for example an interval between one to forty-eight hours, or between one to twelve hours. However, a purge period may be less than one hour due to security and privacy concerns, such as between one and forty-five minutes, or any time interval from five to thirty minutes.

After a timer for an emergency data purge has expired, and if no new requests for the emergency data pertaining to the particular user and the particular electronic device 160, or other devices associated with the user, are received, the emergency data manager 100 may mark any particular related database entries for deletion and wait for another, different, time-out interval. After a particular second time-out interval has also been completed, and if no new requests for emergency data for the particular user or associated electronic devices 160 are received, then the emergency data manager 100 may remove the specific marked entries from the databases in the next cycle of database updates.

After adding the emergency data in a database such as protected data database 191, the emergency data manager 100 may proceed to keep updating the emergency data on a periodic, or as-needed basis. In other words, the data regarding a user or electronic device 160 is kept current such that the most recent and accurate emergency data can be provided to emergency responders. The emergency data manager 100 is updated with emergency data from devices 160, and/or databases 120, for all the emergency data pertaining to all users and their associated electronic devices 160. As an alternative to having a purge period defined by a timer, a purge period may be based on an on-going emergency session such as an emergency call. For session-based purging, emergency data may be deleted after the emergency session has been terminated. To further ensure that the specific emergency data is no longer required, session-based emergency data purging may be performed after a predetermined time delay following emergency session termination, such as a time delay of between one and fifty minutes. A time delay is also beneficial in the case of dropped calls, follow-up calls, etc.

In some non-emergency situations, there is a need to access location data, user data, emergency data or sensor data. For example, a user of an electronic device 160 may grant authorization to family members to access the user's location data. Accordingly, if a family member requests location data for a user, access is granted if there is proper authorization. In another example of location data access, an employee may be required to share location data with an employer, for example through a corporate operations center, such that the corporate operations center is notified when the employee is in an emergency. In another example, a taxi operations company may request and obtain location data of one or more fleet members to keep track of its vehicles, for example, via an onboard vehicle console or terminal. All of these emergency data accesses are monitored by the emergency data manager 100 and are subject to proper authentication credential before being provided.

Figure 4:
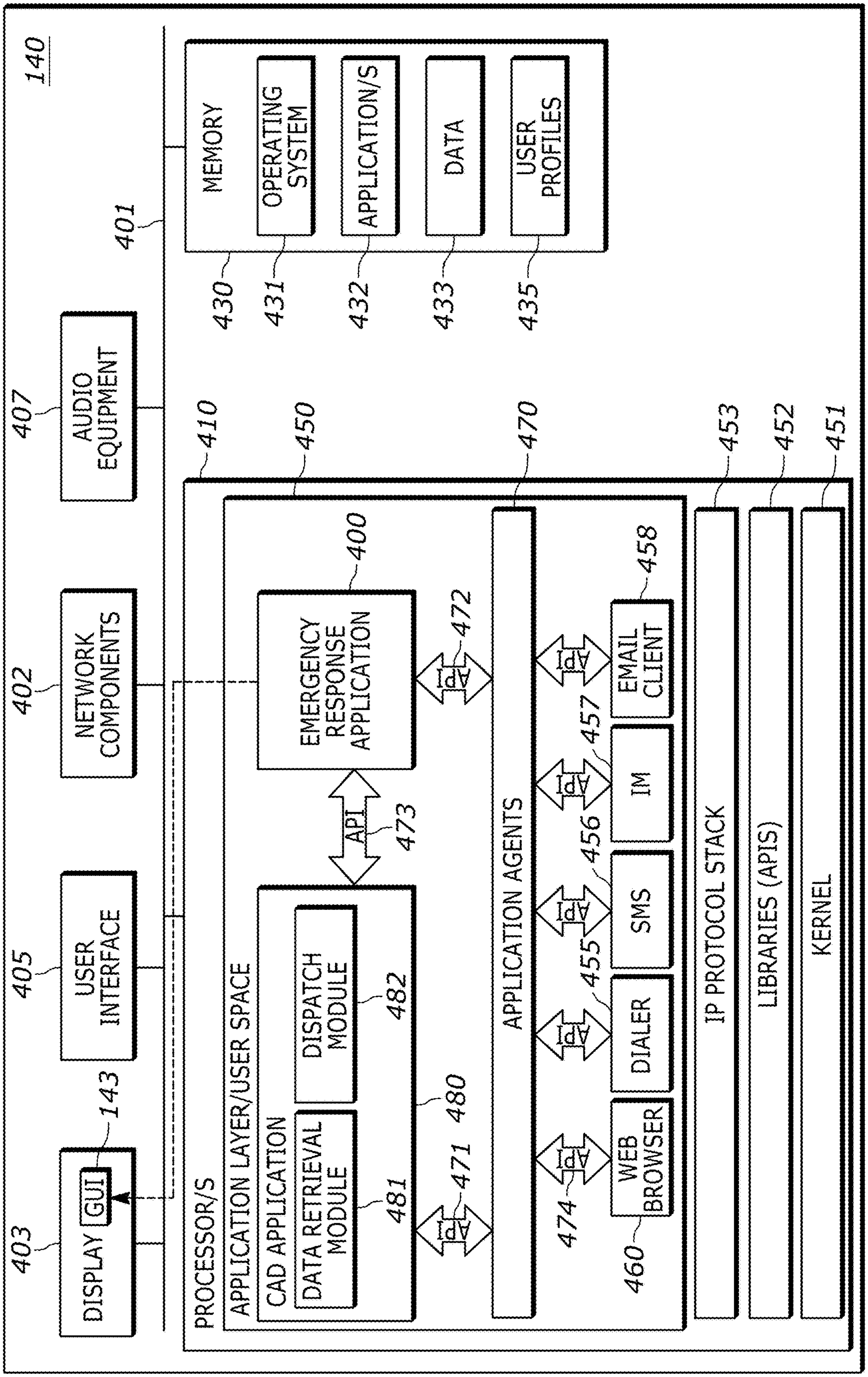
FIG. 4 is a diagram of an example emergency network entity having an emergency response application in accordance with one embodiment.

FIG. 4 provides an example emergency network entity 140 which is a computer aided dispatch (CAD) workstation and is one example of an emergency network entity. An emergency network may be implemented with multiple emergency network entities of various kinds and therefore may have multiple workstations for example one or more call handling workstations, one or more CAD workstations, etc., in addition to routers, switches, hubs, access points, and other emergency network entities, etc. The example CAD emergency network entity 140 may include a display 403, a user interface 405, audio equipment 407, network components 402, at least one processor 410, and at least one non-volatile, non-transitory memory 430 in addition to RAM. All of the components of the emergency network entity 140 are operatively coupled by an internal communication bus 401. The network components may include one or more network transceivers for Ethernet connectivity to other workstations and devices and an Internet connection. The memory 430 stores executable instructions and data such as executable instructions for an operating system 431 and various applications 432. The memory 430 also stores data 433 which may provide data caching. User profiles 435 store emergency network personnel profiles including login credentials for authorized users of the emergency network entity 140.

The processor 410 may be implemented as one or more microprocessors, DSPs, ASICS, FPGAs, microcomputers, microcontrollers, digital signal processors, central processing units, state machines, logic circuitries, and/or devices that manipulate signals based on operational instructions. Among other capabilities, the processor 410 is configured and operative to fetch and execute computer-readable instructions (i.e. executable instructions) stored in the memory 430. For example, the applications 432 executable instructions, when executed by the at least one processor 410, may provide an operating system, a dialer application 455, a short-message-service (SMS) application 456, an instant message (IM) application 457, a web browser 460, an email client 458 and one or more instant message (IM) and voice applications which may each provide IM and voice call capability separately or in combination. The operating system may include a kernel 451, libraries 452 (also referred to as "application programming interfaces" or APIs), an IP protocol stack 453, and an application layer 450 or user space within which the various applications are executed.

In the example emergency network entity 140 of FIG. 4, the applications 432 executable instructions, when executed by the at least one processor 410, provide a standalone emergency response application 400 with associated GUI 143, a computer aided dispatch (CAD) application 480 including an data retrieval module 481, a dispatch module 482, and an associated GUI 142 described in FIG. 1. In the example implementation illustrated in FIG. 4, the emergency response logic 144 shown in FIG. 1 is operatively implemented as the standalone emergency response application 400 in accordance with an embodiment.

The standalone emergency response application 400 is operative to communicate with the emergency data manager 100 and to request emergency data such as medical data and other emergency data which may be protected data. For example, an API 472 enables communication between the emergency response application 400 and the IP protocol stack 453. Application agents 470 may also enable communication between the emergency response application 400 and other applications such as the web browser 460 which uses an API 474. The CAD application 480 may also communication with other applications using an API 471, and with the emergency response application 400 via an API 473.

The GUI 143 of the emergency response application 400 is operative to communicate with the emergency data manager 100 to send emergency data queries using a device identifier, and also to receive emergency data that is pushed to the emergency response application 400 by the emergency data manager 100. The UAV dispatch controller 300 and UAV medical equipment controller 380 also communicate with the emergency response application 400 to provide UAV dispatch capabilities for each emergency in a queue of emergency events provided to the emergency response application 400 by the emergency data manager 100.

The emergency response application 400 provides the GUI 143 on the emergency network entity display 403, and displays augmented emergency data such as, but not limited to, augmented location data received from the emergency data manager 100, and sensor data related to alarm events in an alarm queue. Communication is established between the emergency response application 400 and the emergency data manager 100 using the IP protocol stack 453 and a network connection is established which may be a TCP connection and which may include one or more WebSocket connections.

Figure 5:
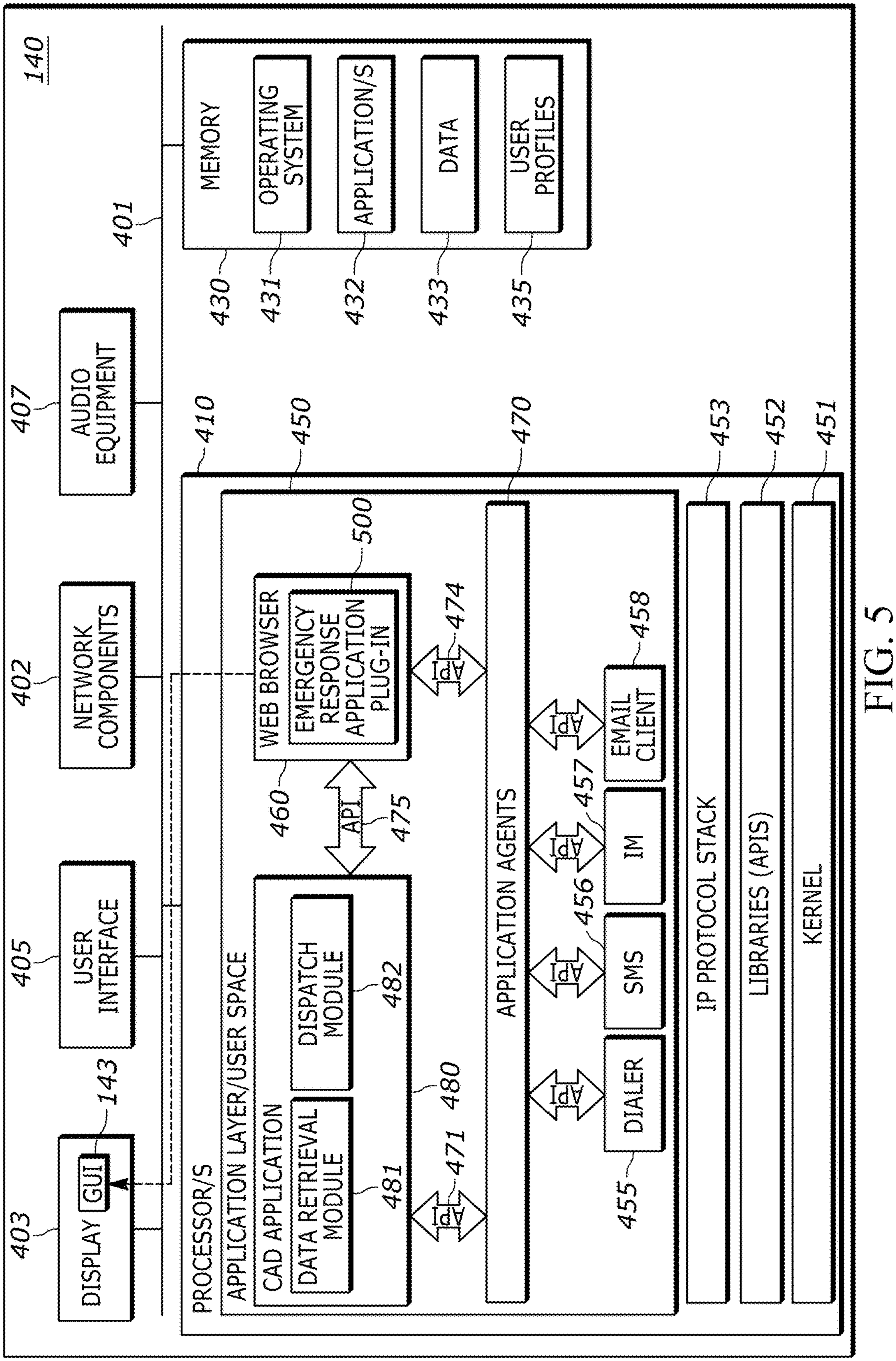
FIG. 5 is a diagram of an example emergency network entity having an emergency response application plug-in accordance with one embodiment.

FIG. 5 is a diagram illustrating another example emergency network emergency network entity 140 having an emergency response application plug-in 500 with a Web browser 460 in accordance with another embodiment. In the example implementation of FIG. 5, the Web browser 460 communicates with the emergency data manager 100 to provide the GUI 143 as a SaaS interface. In other words, the emergency response application plug-in 500 is operative to use an established IP protocol stack 453 connection between the emergency network entity 140 and the emergency data manager 100 using the Web browser 460. The emergency response application plug-in 500 is operative to receive pushed emergency data from the emergency data manager 100 and display the emergency data on the GUI 143. The emergency response application plug-in 500 in conjunction with the Web browser 460 also enables emergency data queries to the emergency data manager 100 to obtain emergency data, in addition to any emergency data received via a push operation. In some embodiments, the emergency response application plug-in 500 may communicate with the CAD application 480 via an API 475 to send and receive data such as, but not limited to, ALI/ANI (Automatic Location Identification/Automatic Number Identification) data, ELS data, AML data, etc. An emergency data query sent to the emergency data manager 100 by the emergency response application plug-in 500 may utilize one or more WebSocket connections.

Figure 6:
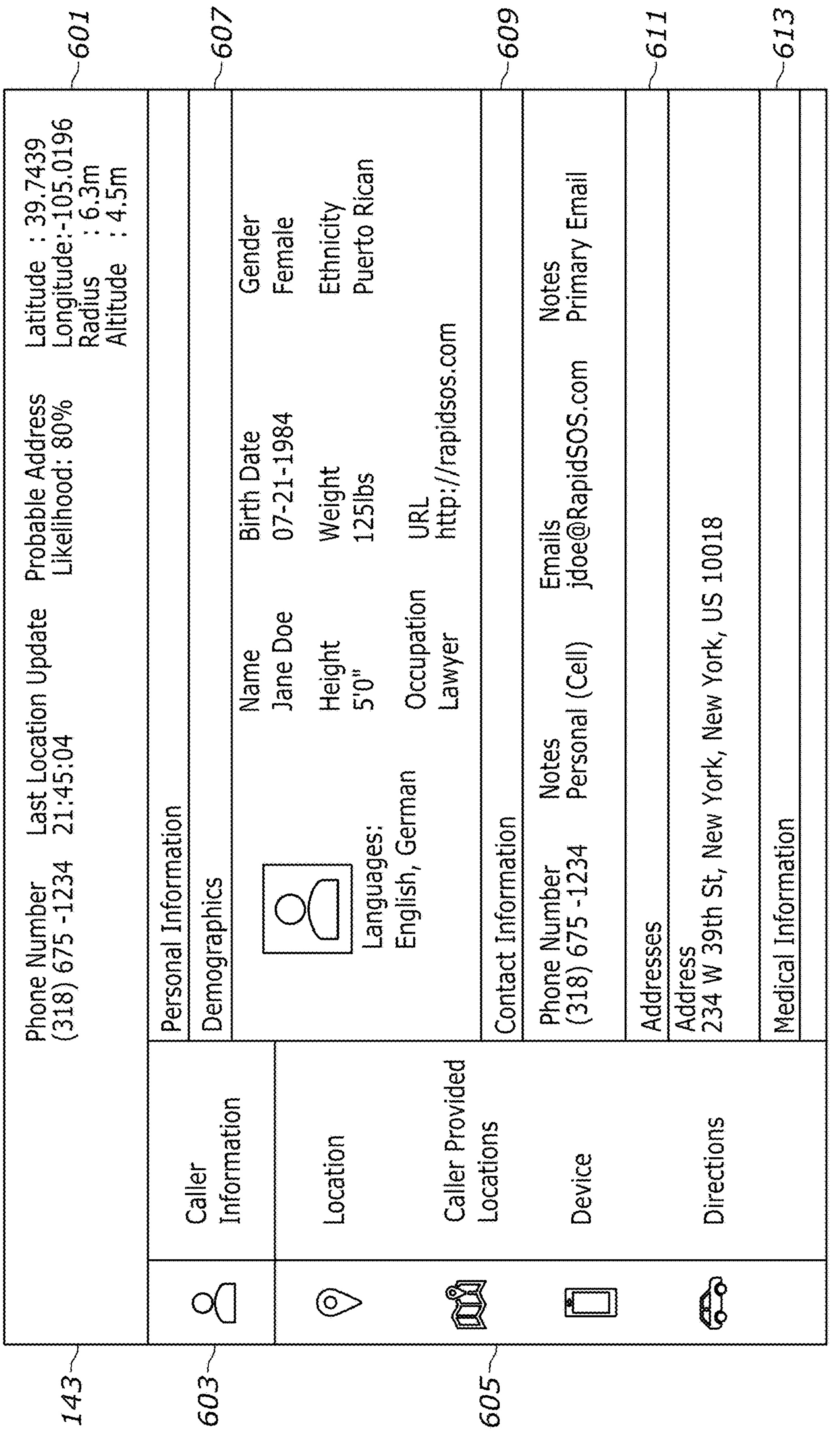
FIG. 6 is an example graphical user interface (GUI) displayed on an emergency network entity display in accordance with an embodiment.

An example of the GUI 143 displayed on an emergency network entity 140 display is shown in FIG. 6. Emergency data sent to the GUI 143 by the emergency data manager 100 may include information such as, but not limited to: service data reference, full name, email, emergency contacts, addresses, language, occupation, phone numbers, websites, gender, height, weight, ethnicity, profile picture, allergies, medical conditions, medications, disabilities, blood type, medical notes, birthday, and additional comments. The emergency response application GUI 143 displays information included in the emergency data associated with a device identifier as depicted by FIG. 6. An emergency network entity 140 user can access the page displaying the additional information by selecting an additional information button or tab within the GUI 143.

As shown in FIG. 6, the GUI 143 displays emergency data returned from the emergency data manager 100 within discrete emergency data categories in separate data fields. For example, the GUI 143 may include a location field 601, a demographics field 607, a contact Information field 609, an addresses field 611, and a medical information field 613. The "Demographics," "Contact Information," and "Addresses" emergency data categories are displayed sequentially under a "Personal Information" section of the GUI 143. A Medical Information field 613 is displayed below the Personal Information section. The GUI 143 may include one or more tabs to filter emergency data categories. For example, as depicted in FIG. 6, GUI 143 can include a "Caller Information" tab 603, and a menu 605 including a "Location" tab, a "Caller-Provided Locations" tab, a "Devices" tab, and a "Directions" tab. A "Directions" tab can be selected within the GUI 143 to render a map displaying directions from a PSAP to a location of an emergency situation. The map is capable of providing real-time or near real-time traffic updates.

Figure 7:
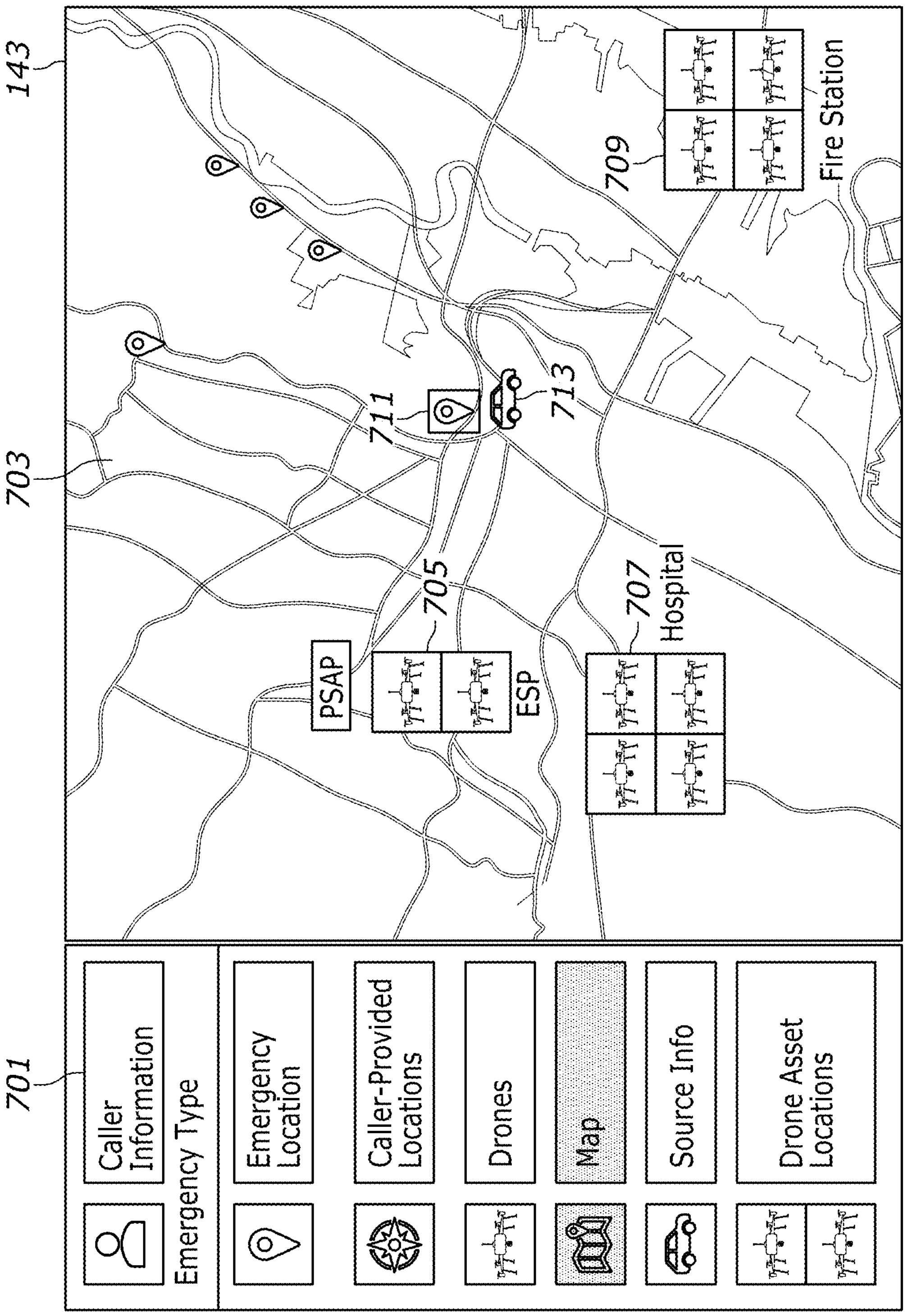
FIG. 7 is another example graphical user interface (GUI) displayed on an emergency network entity display in accordance with an embodiment.

FIG. 7 depicts a GUI 143 provided by the emergency response application during UAV dispatch operations. For a given emergency type, such as a medical emergency where a patient is undergoing diabetic shock, a heart attack, etc., a UAV can be deployed to the patient location and can provide a medical equipment payload such as insulin, a defibrillator device, etc., in order to provide rapid care to address the medical condition of the patient. A UAV, also referred to as a drone, may be a vehicle or device such as multi-rotor aircrafts including helicopters, tricopters, quadcopters, hexacopters, octocopters, etc. A UAV may also be fixed-wing aircraft such as airplanes, rotary-wing aircraft such as helicopters, etc. or other types of drones such as water vehicles (e.g., boats, ships, submarines, etc.) or motor vehicles (e.g., cars, trucks, etc.), etc.

In FIG. 7 an emergency network entity operator can view data for a UAV dispatch to an emergency location. In the example GUI 143, a left side menu 701 provides a "caller information" selection that displays information associated with the caller and emergency type, an emergency location selection, caller-provided location selection, drone information selection source information selection and UAV (drone) asset location selection. The right side of the GUI 143 is a geographical map that displays a location indicator 711 showing the emergency location, a first UAV asset location 705 at a PSAP, a second UAV asset location 707 at a hospital, and a third UAV asset location 709 at a fire station. A location indicator 713 showing the location of the of the calling device is also displayed.

Each of the UAVs may be configured with various capabilities, equipment, sensors, etc., such as cameras, microphones, thermal cameras, etc., to enable certain surveillance capabilities ("surveillance drones"). Other drones can be configured to carry and/or deliver supplies such as medical supplies, fire supplies, other utility supplies, etc. ("response drones").

The emergency response logic 144 together with its respective emergency network manager at the emergency data manager 100, monitor an emergency queue of emergency calls, alarms and alerts that each require a response. The emergency data manager 100 may automatically determine emergency type when possible based on available data, such as fire, medical, police, HAZMAT etc. Based on the emergency type and in some implementations, as severity level, a UAV may be automatically dispatched by the emergency data manager 100 and a data feed provided to the GUI 143 as shown in FIG. 7.

The emergency data manager 100, via the emergency network managers 379, determines UAV or drone "availability." The availability is determined based on various factors, parameters, etc. For example, the time to reach the emergency location (ETA), battery remaining in the drone, type of camera (imaging and/or thermal), microphone, capacity of the payload of the drone, type of payload, etc., are all accounted for in making the determination of availability for a given emergency type.

Figure 8A:
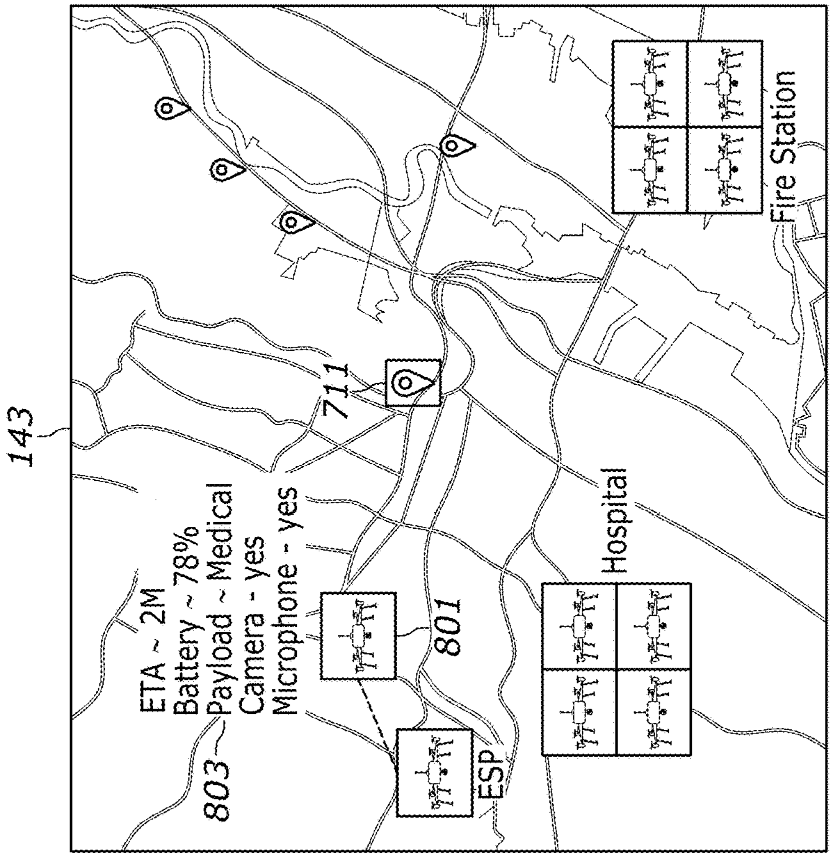
FIG. 8A and FIG. 8B provide another example graphical user interface (GUI) displayed on an emergency network entity display in accordance with an embodiment.
Figure 8B:
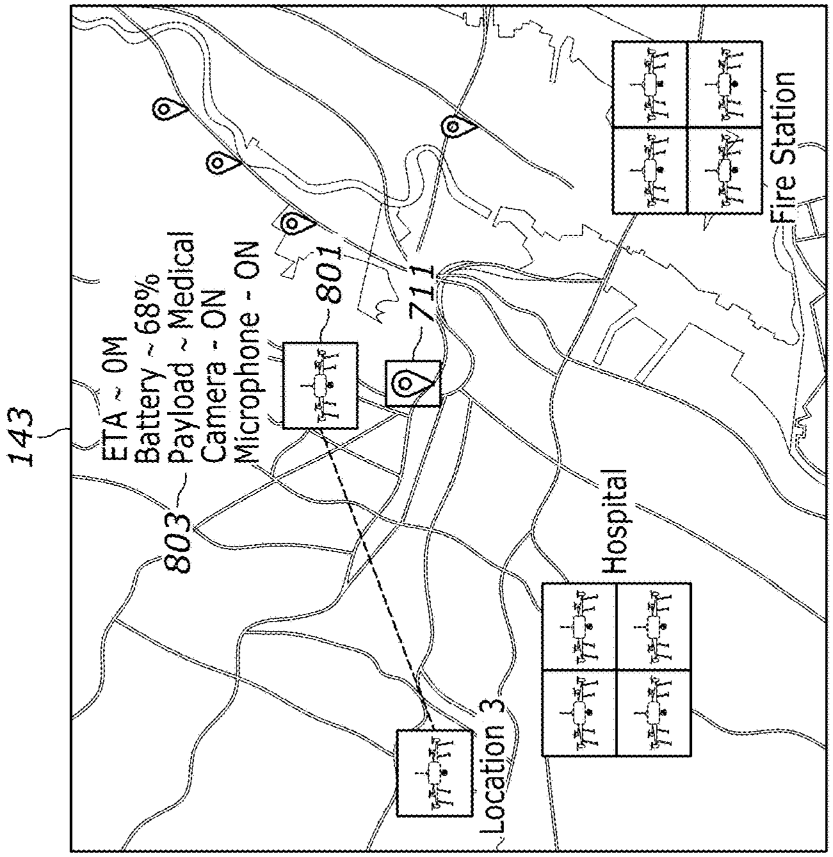

FIG. 8A and FIG. 8B illustrate how the GUI 143 is updated real time during UAV dispatch and deployment. In FIG. 8A, after a given UAV is dispatched, a UAV indicator 801 shows is position on the GUI 143 map view. The status 803 of the UAV is also shown including ETA, battery status, payload type, and other capabilities such as visual and audio. FIG. 8B is a view after the UAV is arriving at the emergency location, shown by emergency location indicator 711. The UAV indicator 801 moves to the new position and the status 803 is accordingly updated.

Figure 9:
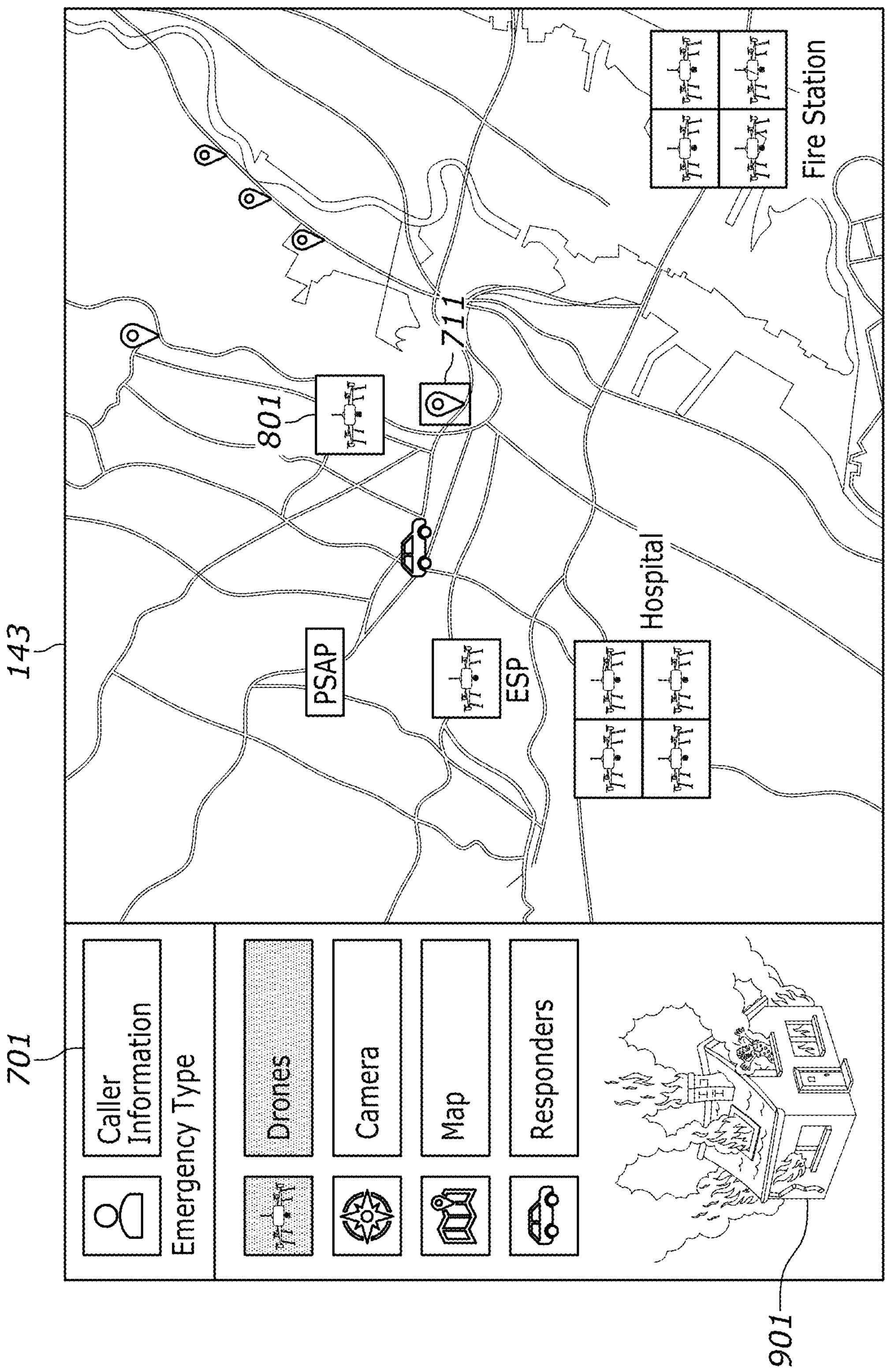
FIG. 9 is another example graphical user interface (GUI) displayed on an emergency network entity display in accordance with an embodiment.
Figure 10:
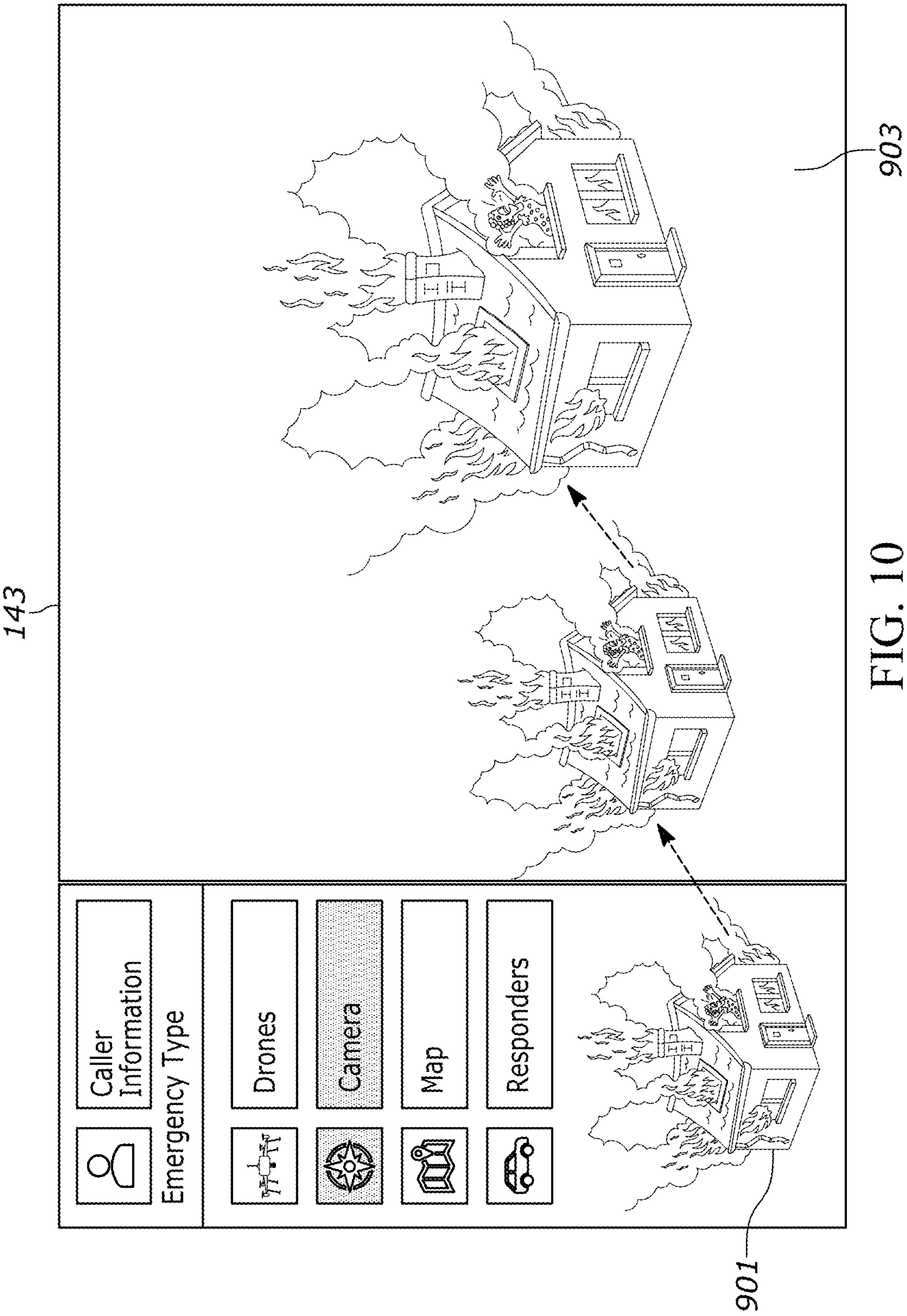
FIG. 10 is another example graphical user interface (GUI) displayed on an emergency network entity display in accordance with an embodiment in which a UAV provides video data to the emergency network entity display.

FIG. 9 shows an updated GUI 143 upon receiving video surveillance data from the UAV. In the example GUI 143 shown in FIG. 9, the UAV video feed 901 appears in the left side menu 701. Based on the emergency site images, real-time video feed, and other inputs received from the first UAV, the emergency network entity operator may determine whether to dispatch additional UAVs and/or other resources. FIG. 10 illustrates the GUI 143 when the emergency network entity operator performs a drag-and-drop of the UAV video feed 901 into the map area to provide expanded UAV video feed 903. In a fire emergency as depicted, the surveillance UAV may be able to locate a fire in a building and identify persons in need of emergency assistance.

UAVs may be equipped with one or more sensors. Sensor data from the UAV may be transmitted via the control link to the emergency network entity. The UAV sensor data may be sent by a UAV to the UAV base station 203 and an emergency network entity retrieves the sensor data from the UAV base station 203 via the control link.

As used herein, "sensor data" refers to information obtained or provided by one or more sensors. A sensor may be associated with a device for example, a sensor may be internal or externally paired with a UAV. Sensor data may be relevant to an emergency situation such as heart rate during a cardiac emergency event. A sensor and/or sensor device may be, but is not limited to, an acoustic sensor, a breathalyzer, a carbon dioxide sensor, a carbon monoxide sensor, an infrared sensor, an oxygen sensor, an ozone monitor, a pH sensor, a smoke detector, a current sensor (e.g., detects electric current in a wire), a magnetometer, a metal detector, a radio direction finder, a voltage detector, an air flow meter, an anemometer, a flow sensor, a gas meter, a water meter, a Geiger counter, an altimeter, an air speed indicator, a depth gauge, a gyroscope, a compass, an odometer, a shock detector, a barometer, a pressure gauge, a thermometer, a proximity sensor, a motion detector, an occupancy sensor, or any combination thereof. Sensor data may be obtained from any of these types of sensors.

One or more sensors may be external to a UAV, but physically attached to the UAV. A UAV may transmit sensor data via one or more control links to the UAV base station 203. The one or more sensors may provide or send sensor data to the UAV autonomously, for example via Bluetooth™.

Use of UAVs can be used by emergency responders for responding to fire emergencies. By identifying the scope and spread of a fire by surveillance, data from a UAV (camera feed, temperature, smoke sensors, etc.) can provide situational awareness about the emergency. For example, if a fire alarm has been pulled, but there is no smoke or evidence of fire, it may be a false alarm. In the case of structural fires, the camera feed from the UAV can be used to determine the approach to the scene by emergency responders. In addition, fire-fighting drones can also be deployed to apply extinguishing at strategic targets, even if they are not easily accessible.

Figure 11:
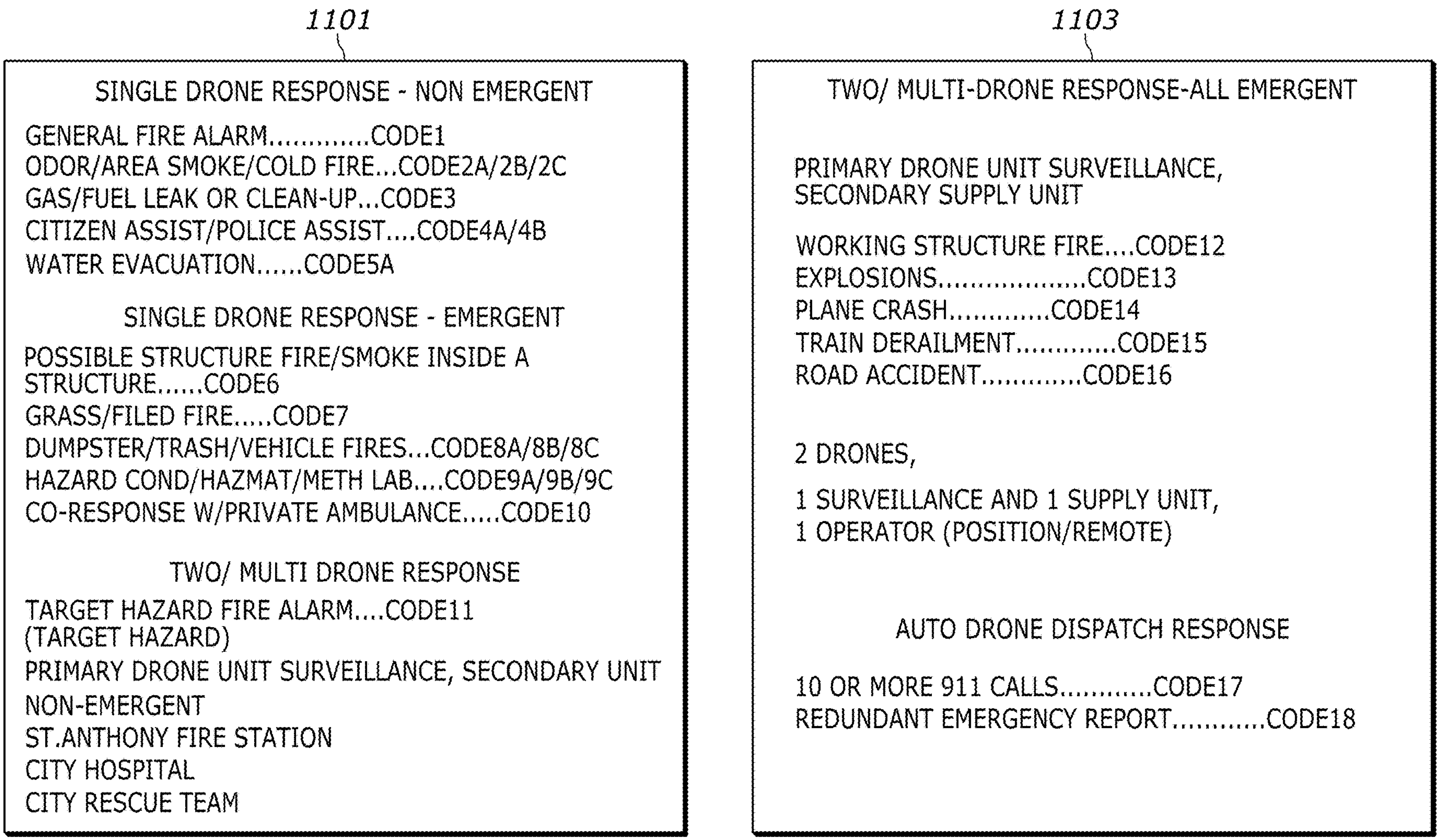
FIG. 11 is an example of UAV response codes in accordance with various embodiments.

FIG. 11 depicts example protocols to be used and/or implemented in generating a UAV dispatch recommendation in various scenarios or for automatic UAV dispatch by the emergency data manager 100 for a given emergency type meeting the given criteria. Using the example protocols, a UAV may be dispatched for surveillance and/or response for emergencies such as, but not limited to, a building fire, a person having a heart attack, a robbery in-progress, a roadblock during a medical emergency, a victim of a got shot who is losing blood, etc. However, UAVs may also be dispatched for non-emergency situations also as shown.

UAVs may be auto-dispatched by the emergency data manager 100 and auto-dispatch settings may be setup for each emergency network entity using the GUI 143. For example, the settings may allow auto-dispatch only for certain types of emergency, such as fires, gunshot detections, etc. A setting may also require that the emergency network entity operation confirm that a UAV should be deployed prior to auto-dispatch. In auto-dispatch, the emergency data manager 100 determines the emergency type based on emergency data it has received associate with an emergency call, alarm or alert, along with location data. An appropriated UAV is determined based on availability. Availability is determined by ETA of the UAV to the emergency location, UAV battery charge available, UAV payload if required, UAV sensor capability, etc. If a UAV is available, the emergency data manager 100 sends emergency location data over the UAV control system (i.e. the UAV dispatch controller 250, UAV radio controller 200 and UAV base station 203) and the UAV uses its onboard GPS module 270 and the emergency location data. The programmable flight controller 294 auto-navigates the UAV to the emergency location and either hovers in place or lands if a payload is present. Once the UAV is at the emergency location, the emergency network entity operator is able to take over control of the UAV via the GUI 143. The emergency network entity operator has the option to take over control of the UAV at any time, even during the auto-dispatch/auto-navigation operation. When the UAV has completed its mission, the emergency network entity operator can activate a "home" button on the GUI 143 for that particular UAV, and the flight controller 294 will auto-navigate the UAV back to its home base without any need for action by the emergency network entity operation. The UAV will land and dock at its home base location.

UAVs may be deployed after making a severity determination about the emergency. A severity scale from 1-10 may be used as a severity score. In some cases, when the emergency is more severe, emergency responders may be preferred over deploying UAVs. For example, severity scores below 5 may be the ones in which a UAV may be deployed. For example, when the emergency is more severe, emergency responders may be preferred over deploying UAVs. In that case, the auto-dispatch operation will not occur and the emergency network entity operator will handle that specific emergency using other defined dispatch procedures.

In some implementations, the audio equipment 292 on a surveillance UAV can be configured to detect audible "chatter" around the emergency location. Such audio content can be processed using speech processing, natural language processing (NLP) and/or artificial intelligence to identify keywords like "heart attack," "blood," "medical," "hospital," "ambulance." etc. Such processing and/or determination of emergency may be done by personnel utilizing the mentioned speech processing techniques and/or as part of emergency type determination by the emergency data manager 100. Keywords such as "heart attack," "blood," "medical," "hospital," "wound," "hurt," etc. can lead to a determination that a medical emergency is occurring.

As used herein, "emergency data" refers to data pertaining to an on-going or historical emergency. The emergency data may be generated at the time of the emergency, or before the emergency occurs and may be made accessible when the emergency occurs. One type of emergency data is location data, which provides a current location of an emergency which often times will be based on the location of a user device. Because of privacy and security concerns, emergency data must be stored, accessed, and transmitted using security and privacy measures.

The dispatched UAVs may carry a payload with supplies, equipment, etc. that may be advantageous in addressing the type of emergency that is occurring. Such supplies can, for example, assist a first responder (if the responder is on site) or any other medical professional/practitioner on the site to save the life of the victim in case of medical emergency by providing the supplies required. Examples of such supplies that can be supplied by the referenced response UAV include blood, first aid kit, defibrillator kit, AED kit, epinephrine auto-injector etc. In some implementations, a screen or other such interface mounted on a UAV can be configured to display, project, and/or otherwise output content that reflects instructions regarding first aid procedures and other emergency-related content, including how to use available medical supplies to help the victim.

The UAVs can also be used to assist an emergency network in determining the identity of the victim during a medical emergency (e.g., using face recognition). For example, the drone can be configured to execute an application through which connections can be established with the user's available devices, e.g., to determine vital signs and/or other health information from the user's devices (smartphone, smartwatch, wearable device, etc.). For example, a secure connection can be established between the user's devices and the emergency network entity GUI 143 and medical information can be obtained the before the battery drains out. The collected medical information can be supplied to the emergency network entity GUI 143 along with determined physical conditions of the victim. Based on the information collected from the referenced user device(s) and any other health information stored on these devices, the described technologies can determine the vitals and heath conditions which need urgent attention.

In another example, in case of fire, a drone can initially be dispatched, e.g., to determine the cause of the fire, ignition point of the fire, people trapped inside the building, etc. using infrared/thermal cameras and/or other sensors. The drone can also alert the rescue team, fire station, etc. For example, the GUI 143 can show approach of a first team of emergency responders and their distance from the emergency location, as well as real-time image/video content from drone(s) present at the emergency location.

In some implementations, a drone (e.g., a surveillance drone) can be further configured to assist in a rescue mission and/or other operations. For example, such a drone can be configured to project, broadcast, output, etc. audio or video content in the direction of and/or within a building that is on fire. Doing so can provide instructions for those inside to safely evacuate. Additionally, in certain implementations the described technologies can be configured to enable the referenced drone to illuminate the path way to the exit and/or provide audio directions to follow the path to exit safely.

In some implementations, a severity protocol can be defined. Various factors associated with such a determination are depicted in FIG. 11, along with aspects of corresponding response(s) to such incidents. Per the referenced severity protocol, if multiple emergencies are reported from a common area/location, drone assets may be particularly helpful as emergency resources may be stretched and the emergency may be a mass emergency. For example, when many emergencies are occurring (e.g., 10 calls or more from a specific location within a 10-minute interval), the described technologies can be configured to dispatch drone assets (e.g., a surveillance drone fleet), e.g., from a nearby site. Also, if the emergency type has been determined, rescue or response drones with supplies can follow automatically.

Figure 12:
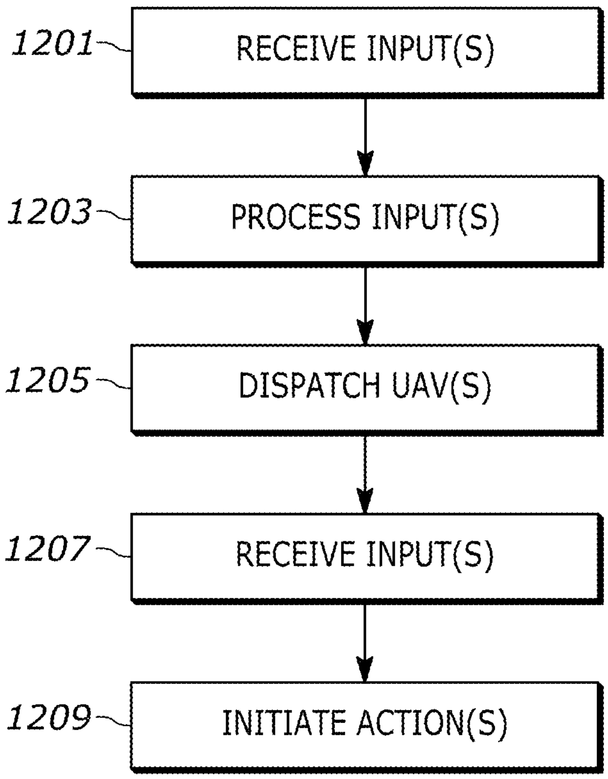
FIG. 12 is a flowchart of a method of operation of an emergency data manager in accordance with an embodiment.

FIG. 12 is a flow chart illustrating a method of operation of the emergency data manager 100 for automated emergency dispatch of unmanned aerial vehicles (UAVs). The method of operation begins and at operation 1201, one or more first inputs are received, from one or more devices. For example, inputs can be received from mobile devices, wearable devices, sensors, cameras, emergency notification buttons/devices, etc. At operation 1203, the one or more first inputs are processed. In doing so, an occurrence and severity of an emergency event can be identified, determined, etc. For example, based on inputs originating from a wearable device, smoke alarm, etc., an emergency associated with a user (e.g., cardiac arrest, diabetic shock, car accident, building fire, etc.) can be identified. At operation 1205, one or more unmanned aerial vehicles (UAVs or drones) are dispatched. In certain implementations, such UAVs can be dispatched based on the identification of the emergency event. Additionally, in certain implementations such UAV(s) can be dispatched to a location associated with the identified emergency event. As described herein, such location can be determined based on the referenced input received (e.g., inputs originating from sensors or interfaces the referenced device(s), such as GPS receivers, communication interfaces, etc.). In certain implementations the referenced UAVs can be dispatched based on various factors. For example, the referenced UAVs can be dispatched based on their respective capabilities (e.g., payload capacity, battery remaining, type of camera (imaging/thermal and/or infrared, night vision), flight time capability, automatic/manual operation, etc.). Additionally, in certain implementations the referenced UAVs can be dispatched based on various determinations computed with respect to the UAVs and/or other resources. For example, respective ETAs can be computed for emergency personnel (ambulances, paramedics, etc.) and for various UAVs determined to be proximate to the location of the emergency. Such ETAs can then be compared to determine which resources are likely to arrive at the emergency soonest. The respective capabilities of such resources can also be accounted for in determining which resources to dispatch, as described herein. At operation 1207, one or more second inputs can be received. In certain implementations, such inputs can be received from the one or more first UAVs dispatched at operation 1205. For example, audio and/or visual content and other information can be captured and provided by the referenced UAVs. Such content can reflect current conditions at the location of the emergency, the health state of a user experiencing the emergency, etc. At operation 1209, one or more actions are initiated. In certain implementations, such actions can be initiated based on the one or more second inputs as received at operation 1207.

In certain implementations, the referenced actions can include emergency operations performed by the one or more first UAVs, e.g., those initially dispatched at operation 1205. For example, such UAVs can provide, present, project, etc., evacuation information, e.g., in a burning building scenario. By way of further example, such UAVs can provide, present, project, etc., emergency medical information, e.g., in a medical response scenario. Moreover, in certain implementations one or more second UAVs can be dispatched to the referenced location. In certain implementations, such second UAVs can be dispatched based on the input received from the first UAVs, e.g., at operation 1207. Additionally, in certain implementations such second UAVs can be dispatched based on their respective capabilities.

For example, upon determining (e.g., based on audio/visual content provided by a first UAV) that a fire, medical emergency, etc., is occurring at a specific location, another UAV having capabilities appropriate for such a scenario (e.g., a payload that includes fire/medical response equipment) can be dispatched to the emergency location. Such a UAV can be further configured to initiate various emergency operations. In doing so, for example, a first UAV can be used to identify or determine aspects of an emergency occurrence, and such determinations can be used to dispatch a second UAV to provide a response, operations, etc. appropriate to such an emergency. Accordingly, multiple UAVs or UAV fleets can be used to identify an occurrence of an emergency (e.g., in a location that may be remote or inaccessible), further determine a type and/or severity associated with such emergency, and initiate deployment of drones.

In one example scenario, one user ("John") can initiate an emergency response (e.g., by dialing 911) to report severe flooding in his area because of excessive rain. Because the rain has not stopped, John was concerned that his neighbors in low-lying areas may have water entering their homes and may be in danger. John also reports that he was getting inconsistent cell phone coverage and others may unable to make emergency calls. The call taker, ("Mary") asks for names and location of the people whose homes may be flooded. John reports that there is an elderly man on the corner house on Corner Street, who has limited mobility and requests emergency assistance for the man, hoping that a patrol of the area might identify others who need help. Mary records information about the emergency from John using the described technologies. Various interfaces (e.g., GUIs as described/depicted herein) can depict (e.g., to Mary) information related to other calls, e.g., those received from other callers from nearby areas.

Upon identifying a number of calls from a particular area about same and/or similar emergency (e.g., above a defined threshold), the emergency data manager 100 can dispatch one or more drones, e.g., from a nearby site, to the emergency location. A notification can also be generated and/or provided to first responders. The inventory of drones and other resources can be updated (e.g., on the GUI 143). Audio/video content can also be provided to the emergency network entity from the emergency site, as described herein.

The referenced audio/visual feed can assist the emergency network entity operator in determining and managing the situation from a control/operation center. Content from a microphone and/or imaging camera on the drone can also provide visual content, chatter, etc. around the emergency site to provide additional context to the situation. Inputs from a thermal camera on the drone can also assist in locating persons in low light conditions. Resources such as responders, supplies, vehicles, etc. can also be dispatched to control the situation.

In the described example scenario, the referenced visual inputs from the drone feed reveal that an electricity power line was seen submerged in the water. Based on such a situation, emergency responders (including drone assets) with appropriate electrical equipment/expertise can be dispatched to contain the submerged wires, patrol the area for other downed lines, etc., for evaluating additional damage.

In another example, the described technologies can be implemented with respect to road accidents causing one or more medical emergencies. For example, several emergency notifications (e.g., emergency calls) can be received by a PSAP, each reporting a multi-car accident on 'Highway 25' with several injuries. Based on such notifications, one or more drones can be dispatched to the location to analyze the situation, as described herein. Other resources, such as fire, medical and police resources can also be dispatched to the location. In some cases, the drone assets will reach the location before other emergency resources can arrive and provide situational awareness for the emergency response. Thus, the drone ('surveillance drone') can capture situational awareness for identifying additional resources that may be necessary.

"Response drones" can be dispatched when they are able to provide appropriate emergency aid. For example, response drones may include a medical payload or other supplies for medical emergencies. Appropriate drone assets may require other components (e.g., sufficient battery power to travel to emergency site and return). As described herein, such drones may connect with or receive instructions from a base station, emergency responders or other drones in the area.

In certain implementations, the described technologies can also be configured to analyze audio content and/or other information captured at or near the site of the emergency. For example, in a multi-car accident scenario, content originating from the drone microphone (and/or other nearby sources) can be processed to detect certain keywords (e.g., "injured," "bleeding," "unconscious," etc.) in the "chatter" occurring near the emergency/accident. Further drones, resources, etc., can be dispatched or otherwise provided with corresponding commands based on audio analysis.

In another example, the described technologies can be utilized during an emergency involving a wildfire. For example, Sally initiates an emergency notification (e.g., an emergency call) to report a fire in a nearby field. Mary, the call taker, prompts Sally to provide information about the emergency location and size of the fire and any persons or pets who might be affected by the fire. Sally indicates that there are some homes on the northwest side of the field that may be affected. Based on the emergency notification, a drone dispatch analysis can be performed to determine if a drone dispatch is appropriate. Drones operated by the PSAP or another facility can be selected and dispatched based on various factors (e.g., based on payload, battery remaining, camera, microphone and thermal camera capabilities). Information from Sally's emergency notification, as well as Mary's notes from the call can be processed together with content captured by a surveillance drones showing a nearby chemical factory. Information from other sources can also be accounted for, reflecting, for example, the location of nearby gas lines. Based on such information and analysis, the described technologies can dispatch resources, (e.g., firemen, trucks, equipment, etc.) to the field to turn off the gas line, stop the spread of fire toward the homes.

In another example, the described technologies can be implemented with respect to a violent attack. For example, in scenarios involving gun violence, the described technologies can dispatch drones to monitor ongoing developments such as the number and location of attackers and victims and type of weapons being used, etc. Emergency resources (e.g., police team, equipment, etc.) can be dispatched to emergency locations based on the information received from the drone. Such resources can be further re-allocated based on updates provided by the drone (e.g., movement of the attackers).

In another example, the described technologies can be implemented with respect to an emergency involving hazardous materials (HAZMAT). For example, an emergency notification (e.g., an emergency call) can be received, reporting a chemical spill originating from a truck that continues to drive on the road. A first drone can be dispatched to capture multi-media content (e.g., audio, images, video) and determine the exact location of the chemical spill, the extent of the spill, etc. Based on the content (e.g., images) received from the first drone, resources such as additional drones (having HAZMAT-related equipment), HAZMAT teams, etc., can be dispatched to the emergency location.

Radio Direction Finding (RDF) for Guiding Drones

In certain implementations, the described technologies can be further configured to route or navigate drone assets to the location of an emergency using various techniques. For example, the described technologies can be configured to route a drone to the location of an emergency signal originating from a "panic button" within a communication device or a standalone emergency notification device (END). For example, using techniques such as radio direction finding (RDF) or similar technology, an antenna embedded or incorporated within the drone can be utilized to receive radio or other signals originating from an emergency notification device.

The emergency (or a specific emergency mode) may be initiated by user input (e.g., pressing of a panic button). In other implementations, the emergency may be initiated by sensor data (e.g., when sensor readings fall outside a threshold range). After the emergency is initiated, an emergency signal may be transmitted to one or more recipients. The alarm signal may be broadcast in a dedicated spectrum (e.g., spectrum for law enforcement, etc.) at a specific frequency (e.g., 800 mHz). The alarm signal may be produced in short pulses in order to conserve battery. An additional power source may be available to the END in the emergency mode (e.g., a crank shaft).

Various information may be transmitted in the alarm signal. For example, the alarm signal may include an identifier of the END (e.g., radio ID), and may include emergency data such as location data, user data (e.g., badge number of the user of the END)), sensor data (e.g., heart rate of the user of the END)), etc.

For example, a mobile radio may send out an emergency signal when a panic button is pressed. The emergency signal may be received by the command center or other mobile radios in the vicinity. In that case, a surveillance drone may be automatically dispatched to the emergency location. Various factors may be taken into account before dispatching drone assets including weather conditions (clear weather preferred), wind speed, battery charge, drone radius, etc. During low light conditions, the drone may include a light attachment for navigation, but this may increase battery usage.

In certain implementations the drone may be guided by various methods. By measuring or determining the signal strength of the emergency signal, the drone using a single antenna may be able to locate the emergency notification device for surveillance or providing emergency response. The drone may be able to utilize other antennas for triangulation, e.g., other drones that are part of the fleet, ground-based antennas, etc.). For example, ground based antennas can be used to direct the drone through larger distances while the single antenna on the drone may be able to fine tune the position by measuring the signal strength from the END. The sensitivity of the radio on the drone and the strength of the alarm signal from the END could be increased for improved locationing capabilities and may be optimized based on power consumption.

The drones may include a software defined radio (SDR) for navigation, that can be configured to both receive and transmit on a certain spectrum (which could be tuned to the frequency of the alarm signal from the END. For example, upon determining an area or location at which the emergency is at maximum strength, the drone can be configured to hover over such area, thereby enabling multimedia content to be captured, and/or other operations to be performed. As used herein, software defined radio (SDR) refers to a radio communication system where hardware components have been implemented through software on computing devices such as computers, mobile phones, mobile radios or other devices. An example SDR system includes a computing system with an analog-to-digital convertor (e.g., a sound card) with an RF front end. An SDR can be integrated into the computing system of the UAVs on individual drones or the base station computer.

Moreover, in certain implementations the described technologies can be configured to initially direct or navigate a drone to a first location, e.g., based on a fixed location API (e.g., generating flying/navigation instructions based on GPS coordinates). For example, a drone may be initially routed to an emergency location based on GPS coordinates. Upon arriving at the referenced location, the drone can be further configured to utilize the referenced radio direction finding (RDF) techniques to further navigate or direct the drone to the specific site of the emergency notification devices.

Such technologies may be advantageously employed in numerous contexts, e.g., to locate a hiker lost in the woods, locating stranded people during flooding, etc. Additionally, in certain implementations the described technologies can configure the drone could to turn on a torch light or other such light source in order to illuminate an area or location.

In some embodiments, the emergency data manager 100 via the emergency network managers 379 and the UAV dispatch controller 300 coordinate the various features and operations described herein (e.g., coordinating the dispatch of emergency resources, UAVs, etc., based on inputs received from various sensors, etc.). In some embodiments, the UAV dispatch controller 300 coordinates drone assets including dispatching and monitoring drone surveillance and emergency response.

Figure 13:
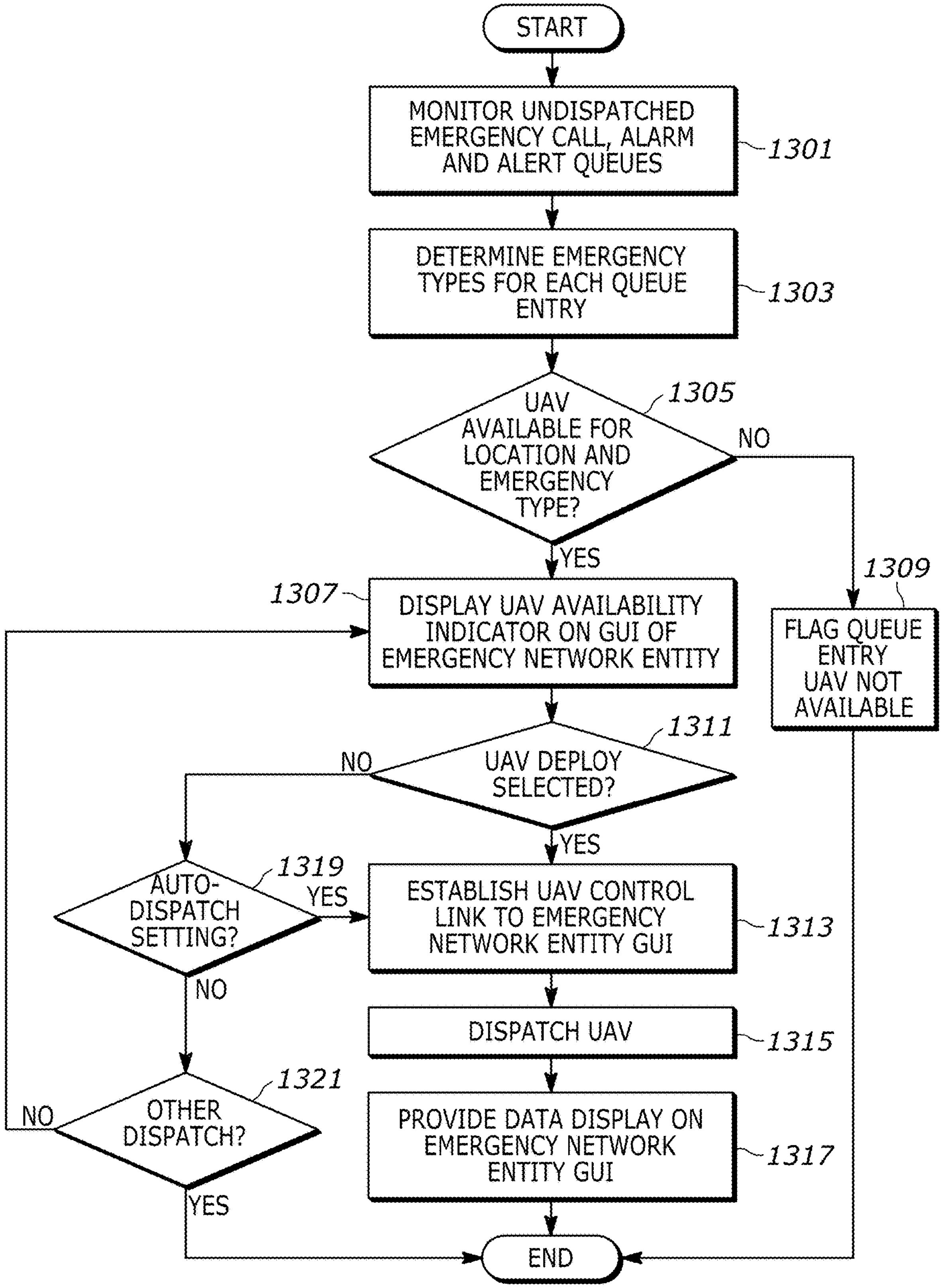
FIG. 13 is a flowchart of a method of operation of an emergency data manager in accordance with an embodiment.

FIG. 13 is a flowchart showing a method of operation of the emergency data manager 100 in accordance with an embodiment. The method of operation begins and in operation block 1301, the emergency data manager 100 monitors on dispatched emergency call alarm and alert queues at an emergency network entity 240. In operation block 1303, the emergency data manager 100 determines the emergency types for each emergency queue entry. At decision block 1305, the emergency data manager 100 determines whether there is a UAV available for the emergency location and the specific emergency type. If a UAV is not available, the emergency data manager 100 will proceed to operation block 1309 and flagged the queue entry that a UAV is not available. This information may be displayed on the GUI 143 on the emergency network entity. The method of operation then ends as shown. However, if a UAV is available at decision block 1305, method of operation proceeds to operation block 1307 and displays an indicator of UAV availability on the GUI 143.

The emergency network entity operator may manually select deployed drone as shown at decision block 1311. Each emergency network entity may also have a setting for auto dispatch of drones based on UAV availability, as shown at decision block 1319. Therefore, if a UAV is not manually deployed at decision block 1311, and the auto dispatch setting is not set decision block 1319, then the emergency data manager 100 will check if any other dispatch operation occurred at decision block 1321. If not, the emergency data manager will wait at operation block 1307 until the specific emergency is cleared from the emergency queue. Up until that time, the emergency network entity operator will have the option of deploying the UAV manually at decision block 1311.

If a manual UAV deployment is selected at decision block 1311, then the emergency data manager 100 will establish a UAV control link to the emergency network entity GUI 143 as shown at operation block 1313. The emergency data manager 100 will then interact with the UAV dispatch controller in operation block 1315 and will dispatch a UAV. In operation block 1317, the dispatched UAV will provide data to the emergency network entity GUI 143. The method of operation then terminates as shown. The emergency network entity operator may terminate operation of the drone by, for example, selecting a return button on the GUI 143 which will cause the dispatched UAV to auto navigate back to its home base. The emergency data manager UAV dispatch controller also constantly monitors the battery status of the dispatched UAV. If the emergency data manager determines that the battery power remaining is becoming insufficient to return the UAV to its home base, the UAV will automatically be returned such that it does not become stranded due to low battery power. In the case of deployment of a medical payload, the medical payload may be left the emergency location. Additionally, in such a low battery condition, and alternative drone may be identified by the emergency data manager and deployed to the emergency location such that it arrives prior to the departure of the UAV having the low battery issue.

If auto dispatch is set decision block 1319, the method of operation will again proceed to operation block 1313 to establish a UAV control link and dispatch the UAV etc. using the same operations as for manual UAV dispatch. If the auto dispatch setting is not set in block 1319, and another dispatch operation has taken place at decision block 1321, for example if emergency responders have already been dispatched location, then the method of operation terminates as shown. However, if needed the emergency network entity operator may at any time manually dispatch a UAV to the emergency location. For example, if the emergency responders request a special piece of medical equipment, a UAV may be deployed to deliver the special piece of medical equipment and a medical payload.

Figure 14:
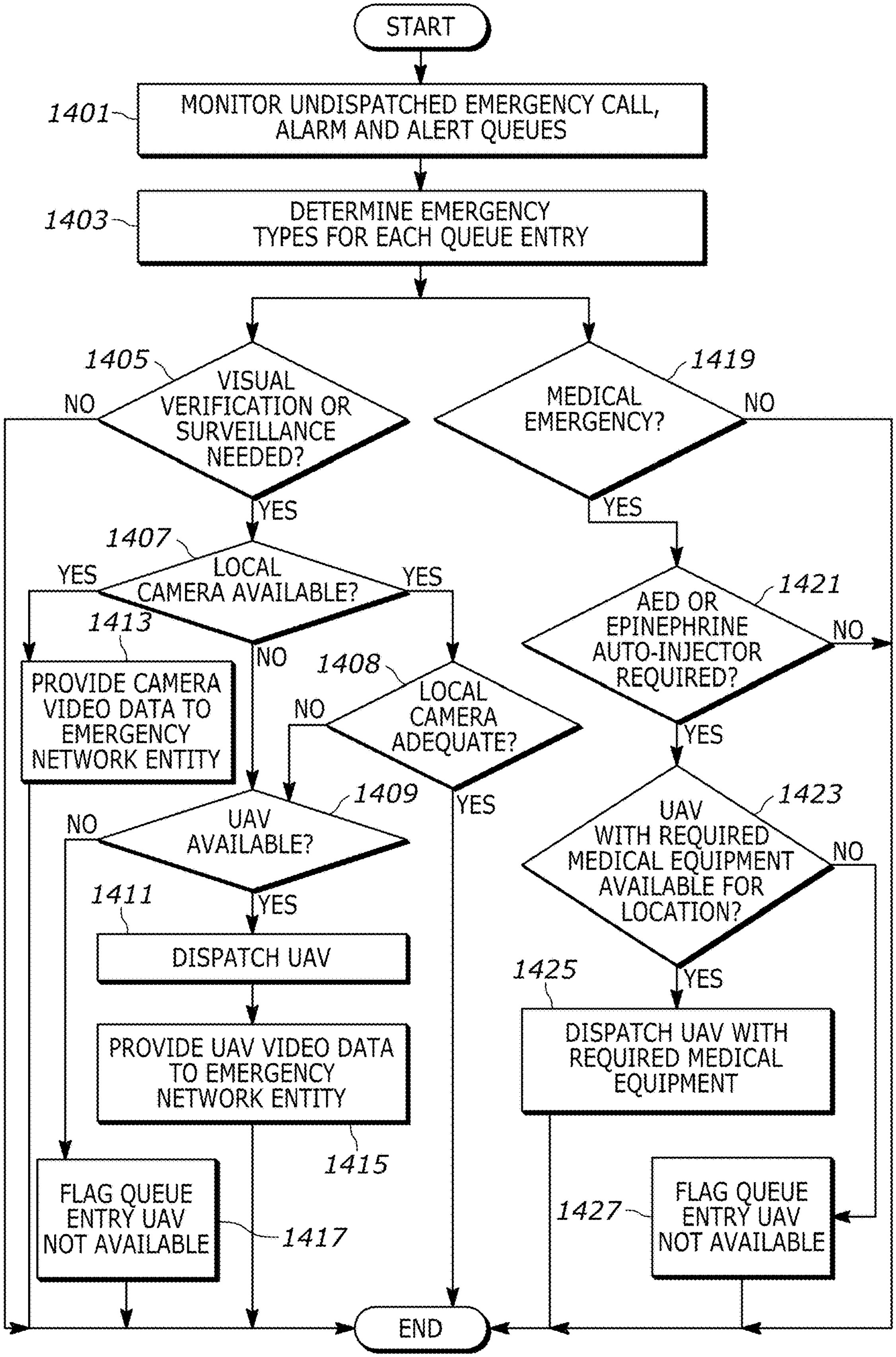
FIG. 14 is a flowchart of a method of operation of an emergency data manager in accordance with an embodiment.

FIG. 14 is a flowchart showing a method of operation of the emergency data manager 100 in accordance with an embodiment. The method of operation begins, and in operation block 1401 the emergency data manager 100 monitors all emergency queues at an emergency network entity. In operation block 1403, for each emergency entry, the emergency data manager 100 determines an emergency type. At decision block 1405, the emergency data manager 100 determines whether the emergency type requires visual verification or surveillance. At the same time, at decision block 1419 the emergency data manager determines whether the emergency type is a medical emergency. If in decision block 1405 no visual verification or surveillance as needed, the method of operation then terminates as shown for that leg of the analysis. Likewise, at decision block 1419 if the emergency type is not a medical emergency, the method of operation then terminates.

If at decision block 1405, visual verification or surveillance is determined to be needed, the emergency data manager proceeds to decision block 1407 and determines if a local camera is available. If a local camera is available, the method of operation proceeds to operation block 1413 and the emergency data manager provides the camera video data to the emergency network entity. However, the emergency data manager also determines whether the local camera video feed is adequate in decision block 1408. If the local camera video feed is adequate, the method of operation terminates as shown. If the local camera is not available in decision block 1407, or if a local camera video feed is not adequate decision block 1408, then at decision block 1409 the emergency data manager 100 determines if a UAV is available. If no UAV is available, the emergency data manager 100 flags the queue entry as UAV not available in operation block 1417, and the method of operation terminates. However, if a UAV is available, then in operation block 1411 the emergency data manager controls the UAV dispatch controller dispatch is a UAV to the emergency location. In operation block 1415 emergency data manager provides the UAV video data to the emergency network entity for display on the GUI 143. The method of operation then terminates and the UAV remains until the emergency network entity operator decides the drone video feed is no longer needed.

Although use of response UAVs for a medical emergency is contemplated below, it is understood that response drones may be used in other types of emergencies. Response drones may be used for providing critical supplies in various emergency types including fire emergencies, car crashes, police emergencies, disaster relief, etc. Use of fire-fighting drones are described in relation to FIG. 9.

UAVs can also be used for providing relief supplies for disaster management. For example, drones may be used to provide relief supplies during epidemics and natural disasters. Various relief supplies such as, but not limited to, drinking water, saline packets, water purification tablets, etc., can dropped off to inaccessible areas by UAVs in flood-affected areas. Personal protective equipment, food, drink or medicines can be dropped off by UAVs in areas affected by an infectious disease epidemic.

In the parallel operation, if a medical emergency is determined to be present at decision block 1419, then in decision block 1421 the emergency data manager 100 determines whether a specific medical equipment item is required such as, but not limited to, an AED or an epinephrine autoinjector. If no special medical equipment is needed, the method of operation terminates. However, if a special medical equipment is needed, then in decision block 1423 the emergency data manager determines if a UAV having the required medical equipment is available for the emergency location. If not, then in operation block 1427 the emergency data manager flags the emergency entry as "UAV not available" and the method of operation terminates. However, if a UAV with the required medical equipment is available, then in operation block 1425 emergency data manager 100 dispatches the UAV with the required medical equipment payload, and the method of operation then terminates. Therefore, two UAVs may be deployed in some emergencies, one for surveillance only, and one to deliver a medical payload.

Figure 15:
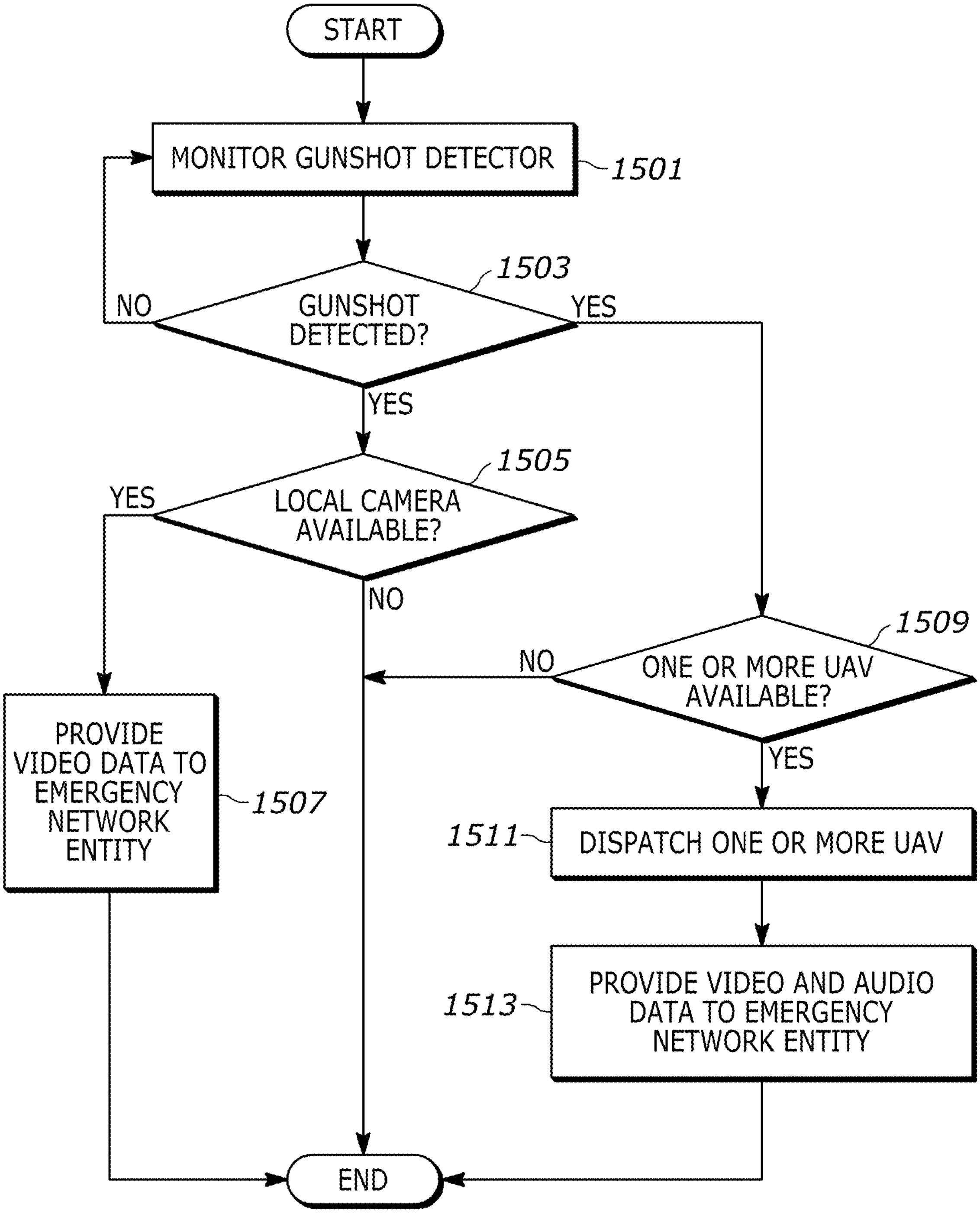
FIG. 15 is a flowchart of a method of operation of an emergency data manager in accordance with an embodiment.

FIG. 15 is a flowchart showing a method of operation of the emergency data manager 100 in accordance with an embodiment. The method of operation begins, and in operation block 1501 the emergency data manager 100 monitors a gunshot detector. If no gunshot is detected in decision block 1503, then the emergency data manager 100 continues to monitor the gunshot detector in operation block 1501. If a gunshot is detected decision block 1503, then the emergency data manager 100 determines if one or more UAVs are available at decision block 1509. If not, method of operation terminates. If one or more UAVs are available, then in operation block 1511 the emergency data manager 100 will dispatch the one or more UAVs, and in operation block 1513 the emergency data manager 100 will provide video and audio data to the emergency network entity.

Additionally, when a gunshot is detected in decision block 1503, in decision block 1505, the emergency data manager will determine whether a local camera is available. If not, that section of the method of operation will terminate. If a local camera is available at decision block 1505, then in operation block 1507 the emergency data manager 100 will provide video data from the local camera to the emergency network entity. That leg of the method of operation will then terminates as shown.

In some implementations, the UAVs themselves may perform the gunshot detector operation. In other words, drones having gunshot detection audio hardware and software may hover over an area having a particular gun violence problem, to perform gunshot detection. Video surveillance information along with audio information subsequent to detecting a gunshot can be provided immediately to an emergency network entity GUI 143 so as to assist in identifying the perpetrator or perpetrators.

While various embodiments have been illustrated and described, it is to be understood that the invention is not so limited. Numerous modifications, changes, variations, substitutions and equivalents will occur to those skilled in the art without departing from the scope of the present invention as defined by the appended claims.

What is claimed is:

1. A method comprising:

monitoring an emergency queue at an emergency network entity;

determining that an emergency type in the emergency queue requires location of a radio signal source;

establishing an unmanned aerial vehicle control link between at least two unmanned aerial vehicles and the emergency network entity;

deploying the at least two unmanned aerial vehicles to a region in which to search for the radio signal source, each unmanned aerial vehicle comprising a radio receiver operative to perform a coordinated location detection operation based on detection of the radio signal;

providing data from the at least two unmanned aerial vehicles on a display of the emergency network entity; and providing an instance of a cloud-based application to the emergency network entity via a cloud-based emergency data manager over an internet connection, the instance comprising a graphical user interface displayed using a web browser executing on the emergency network entity, the graphical user interface comprising the emergency queue and a map view.

2. The method of claim 1, further comprising:

sending emergency location data to the at least two unmanned aerial vehicles from the emergency network entity using the control link.

3. The method of claim 2, further comprising:

auto-navigating by the at least two unmanned aerial vehicles to the emergency location using the emergency location data and an onboard location module.

4. The method of claim 1, further comprising:

providing the map view comprising unmanned aerial vehicle (UAV) location indicators along with operation information for each UAV.

5. The method of claim 1, further comprising:

providing an unmanned aerial vehicle (UAV) control interface to the emergency network entity via the graphical user interface of the instance.

6. The method of claim 5, further comprising:

sending control signals from the UAV control interface in response to input to the graphical user interface of the instance to control the at least two UAVs.

7. An apparatus comprising:

one or more processors; and a non-volatile, non-transitory memory storing instructions that, when executed by the one or more processors, cause the apparatus to:

monitor an emergency queue at an emergency network entity;

determine that an emergency type in the emergency queue requires location of a radio signal source;

establish an unmanned aerial vehicle control link between at least two unmanned aerial vehicles and the emergency network entity;

deploy the at least two unmanned aerial vehicles to a region in which to search for the radio signal source, each unmanned aerial vehicle comprising a radio receiver operative to perform a coordinated location detection operation based on detection of the radio signal;

provide data from the at least two unmanned aerial vehicles on a display of the emergency network entity; and provide an instance of a cloud-based application to the emergency network entity via a cloud-based emergency data manager over an internet connection, the instance comprising a graphical user interface displayed using a web browser executing on the emergency network entity, the graphical user interface comprising the emergency queue and a map view.

8. The apparatus of claim 7, wherein the instructions, when executed by the one or more processors, further cause the apparatus to:

send emergency location data to the at least two unmanned aerial vehicles from the emergency network entity using the control link.

9. The apparatus of claim 8, wherein the instructions, when executed by the one or more processors, further cause the apparatus to:

enable auto-navigation by the at least two unmanned aerial vehicles to the emergency location using the emergency location data and an onboard location module.

10. The apparatus of claim 7, wherein the instructions, when executed by the one or more processors, further cause the apparatus to:

provide the map view comprising unmanned aerial vehicle (UAV) location indicators along with operation information for each UAV.

11. The apparatus of claim 7, wherein the instructions, when executed by the one or more processors, further cause the apparatus to:

provide an unmanned aerial vehicle (UAV) control interface to the emergency network entity via the graphical user interface of the instance.

12. The apparatus of claim 11, wherein the instructions, when executed by the one or more processors, further cause the apparatus to:

send control signals from the UAV control interface in response to input to the graphical user interface of the instance to control the at least two UAVs.

13. The apparatus of claim 7, wherein the emergency network entity comprises a public safety answering point (PSAP) computing device.

14. A non-volatile, non-transitory computer-readable medium storing instructions that, when executed by one or more processors, cause the one or more processors to perform operations comprising:

monitoring an emergency queue at an emergency network entity;

determining that an emergency type in the emergency queue requires location of a radio signal source;

establishing an unmanned aerial vehicle control link between at least two unmanned aerial vehicles and the emergency network entity;

deploying the at least two unmanned aerial vehicles to a region in which to search for the radio signal source, each unmanned aerial vehicle comprising a radio receiver operative to perform a coordinated location detection operation based on detection of the radio signal;

providing data from the at least two unmanned aerial vehicles on a display of the emergency network entity; and providing an instance of a cloud-based application to the emergency network entity via a cloud-based emergency data manager over an internet connection, the instance comprising a graphical user interface displayed using a web browser executing on the emergency network entity, the graphical user interface comprising the emergency queue and a map view.

15. The non-transitory computer-readable medium of claim 14, wherein the operations further comprise:

sending emergency location data to the at least two unmanned aerial vehicles from the emergency network entity using the control link.

16. The non-transitory computer-readable medium of claim 15, wherein the operations further comprise:

auto-navigating by the at least two unmanned aerial vehicles to the emergency location using the emergency location data and an onboard location module.

17. The non-transitory computer-readable medium of claim 14, wherein the operations further comprise:

providing the map view comprising unmanned aerial vehicle (UAV) location indicators along with operation information for each UAV.

18. The non-transitory computer-readable medium of claim 14, wherein the operations further comprise:

providing an unmanned aerial vehicle (UAV) control interface to the emergency network entity via the graphical user interface of the instance.

19. The non-transitory computer-readable medium of claim 18, wherein the operations further comprise:

sending control signals from the UAV control interface in response to input to the graphical user interface of the instance to control the at least two UAVs.

20. The non-transitory computer-readable medium of claim 14, wherein the emergency network entity comprises a public safety answering point (PSAP) computing device.

* * * * *